(12) United States Patent
Kim et al.

(10) Patent No.: US 11,612,348 B2
(45) Date of Patent: Mar. 28, 2023

(54) ELECTRONIC DEVICE EXTENDING SENSING AREA

(71) Applicant: Samsung Electronics Co., Ltd., Suwon-si (KR)

(72) Inventors: Hongki Kim, Suwon-si (KR); Injo Jeong, Suwon-si (KR); Youngjin Oh, Suwon-si (KR); Jungsoo Kim, Suwon-si (KR); Yongsang Yun, Suwon-si (KR); Chijeong Choi, Suwon-si (KR); Seonho Han, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 299 days.

(21) Appl. No.: 16/947,110

(22) Filed: Jul. 17, 2020

(65) Prior Publication Data

US 2021/0015388 A1 Jan. 21, 2021

(30) Foreign Application Priority Data

Jul. 19, 2019 (KR) .................. 10-2019-0087496

(51) Int. Cl.
*A61B 5/30* (2021.01)
*H05K 5/00* (2006.01)
(Continued)

(52) U.S. Cl.
CPC .............. *A61B 5/30* (2021.01); *A61B 5/002* (2013.01); *A61B 5/0006* (2013.01);
(Continued)

(58) Field of Classification Search
CPC ............................. H05K 5/0004; A61B 5/30
See application file for complete search history.

(56) References Cited

U.S. PATENT DOCUMENTS 10,285,643 B2 * 5/2019 Perkins ................ G04B 37/005
10,888,242 B2 * 1/2021 Leabman ............. A61B 5/0004
(Continued)

FOREIGN PATENT DOCUMENTS

JP 2016154754 A 9/2016
KR 10-2016-0058476 A 5/2016
(Continued)

OTHER PUBLICATIONS

International Search Report of the International Searching Authority in connection with International Application No. PCT/KR2020/008919 dated Oct. 20, 2020, 3 pages.

*Primary Examiner* — Hung V Ngo

(57) ABSTRACT

An electronic device includes a housing including a first cover member, a second cover member, and a side member enclosing a space between the first cover member and the second cover member; a support member coupled to or formed integrally with the side member; a printed circuit board disposed in the space and including a biometric circuit; a first conductive portion disposed at least partially in the side member; a second conductive portion and third conductive portion disposed at least partially in the second cover member and electrically connected to the printed circuit board; and at least one conductive path disposed in the space, configured to electrically connect the biometric circuit and the first conductive portion, and formed on the support member. The biometric circuit receives a biometric signal based on the first conductive portion, the second conductive portion, the third conductive portion, and the at least one conductive path.

14 Claims, 32 Drawing Sheets

(51) Int. Cl.
  *H05K 5/03*  (2006.01)
  *H05K 7/14*  (2006.01)
  *H05K 5/02*  (2006.01)
  *A61B 5/00*  (2006.01)

(52) U.S. Cl.
  CPC .......... *A61B 5/0022* (2013.01); *A61B 5/6802* (2013.01); *H05K 5/0004* (2013.01); *H05K 5/0247* (2013.01); *H05K 5/03* (2013.01); *H05K 7/1427* (2013.01); *A61B 2562/12* (2013.01); *A61B 2562/166* (2013.01)

(56) References Cited

U.S. PATENT DOCUMENTS

| | | | |
|---|---|---|---|
| 10,892,565 B2* | 1/2021 | Wei | A61B 5/681 |
| 2011/0071370 A1* | 3/2011 | Al-Ali | A61B 5/72 |
| | | | 600/301 |
| 2015/0280312 A1 | 10/2015 | Poggio | |
| 2015/0309533 A1 | 10/2015 | Majava et al. | |
| 2016/0354036 A1 | 12/2016 | Jo et al. | |
| 2016/0360986 A1* | 12/2016 | Lange | A61B 5/6822 |
| 2016/0367157 A1* | 12/2016 | Blake | A61B 5/053 |
| 2017/0055869 A1 | 3/2017 | Shin et al. | |
| 2017/0215745 A1* | 8/2017 | Felix | A61B 5/7465 |
| 2017/0296088 A1 | 10/2017 | Choi | |
| 2018/0014742 A1* | 1/2018 | Iwawaki | A61B 5/02 |
| 2018/0064363 A1 | 3/2018 | Morun et al. | |
| 2018/0146921 A1* | 5/2018 | Yoon | A61B 5/30 |
| 2018/0212449 A1 | 7/2018 | Park et al. | |
| 2018/0220972 A1 | 8/2018 | Jeong et al. | |
| 2019/0059756 A1 | 2/2019 | Rasmussen et al. | |
| 2019/0131812 A1* | 5/2019 | Lee | G06F 1/163 |
| 2019/0150777 A1* | 5/2019 | Guo | A61B 5/30 |
| 2019/0387984 A1* | 12/2019 | Lin | A61B 5/6841 |
| 2020/0233381 A1 | 7/2020 | Yang et al. | |
| 2020/0405160 A1* | 12/2020 | Nielsen | G01K 13/20 |

FOREIGN PATENT DOCUMENTS

| | | |
|---|---|---|
| KR | 10-2016-0143102 A | 12/2016 |
| KR | 10-1727146 B1 | 4/2017 |
| KR | 10-2017-0118439 A | 10/2017 |
| KR | 10-2018-0088020 A | 8/2018 |

\* cited by examiner

ELECTRONIC DEVICE EXTENDING SENSING AREA

CROSS-REFERENCE TO RELATED APPLICATION

This application is based on and claims priority under 35 U.S.C. 119 to Korean Patent Application No. 10-2019-0087496 filed on Jul. 19, 2019 in the Korean Intellectual Property Office, the disclosure of which is incorporated by reference herein in its entireties.

BACKGROUND

1. Field

Various embodiments of the disclosure relate to an electronic device that extends a sensing area.

2. Description of Related Art

Recently developed electronic devices include various sensors and may include, for example, at least one biometric sensor for measuring biometric information of a user. The electronic device may include a wearable device (e.g., portable watch, portable band, or portable glasses) capable of easily carrying by wearing on a human body. An electronic device equipped with at least one biometric sensor may measure various types of biometric information (e.g., heart rate, electrocardiogram, electroencephalogram (EEG), oxygen saturation, blood pressure, or blood sugar) of a user using the biometric sensor.

The electronic device is gradually becoming slim to easily carry; thus, a sensing area for measuring biometric information may be gradually reduced. As the sensing area is reduced, sensing accuracy for measuring the user's biometric information may decrease.

SUMMARY

Various embodiments of the disclosure may provide an electronic device including a sensing area capable of using at least a portion of a housing thereof as the sensing area.

Various embodiments may provide an electronic device capable of connecting at least one electrode corresponding to a sensing area to a biometric circuit thereof through a conductive path.

According to various embodiments of the disclosure, an electronic device includes a housing including a first cover member, a second cover member facing in a direction opposite to that of the first cover member, and a side member enclosing a space between the first cover member and the second cover member; a support member coupled to or formed integrally with the side member; a printed circuit board disposed in the space and including a biometric circuit; a first conductive portion disposed at least partially in the side member; a second conductive portion and third conductive portion disposed at least partially in the second cover member and electrically connected to the printed circuit board; and/or at least one conductive path disposed in the space, configured to electrically connect the biometric circuit and the first conductive portion, and formed on the support member. The biometric circuit receives a biometric signal based on the first conductive portion, the second conductive portion, the third conductive portion, and the at least one conductive path.

Before undertaking the DETAILED DESCRIPTION below, it may be advantageous to set forth definitions of certain words and phrases used throughout this patent document: the terms "include" and "comprise," as well as derivatives thereof, mean inclusion without limitation; the term "or," is inclusive, meaning and/or; the phrases "associated with" and "associated therewith," as well as derivatives thereof, may mean to include, be included within, interconnect with, contain, be contained within, connect to or with, couple to or with, be communicable with, cooperate with, interleave, juxtapose, be proximate to, be bound to or with, have, have a property of, or the like; and the term "controller" means any device, system or part thereof that controls at least one operation, such a device may be implemented in hardware, firmware or software, or some combination of at least two of the same. It should be noted that the functionality associated with any particular controller may be centralized or distributed, whether locally or remotely.

Moreover, various functions described below can be implemented or supported by one or more computer programs, each of which is formed from computer readable program code and embodied in a computer readable medium. The terms "application" and "program" refer to one or more computer programs, software components, sets of instructions, procedures, functions, objects, classes, instances, related data, or a portion thereof adapted for implementation in a suitable computer readable program code. The phrase "computer readable program code" includes any type of computer code, including source code, object code, and executable code. The phrase "computer readable medium" includes any type of medium capable of being accessed by a computer, such as read only memory (ROM), random access memory (RAM), a hard disk drive, a compact disc (CD), a digital video disc (DVD), or any other type of memory. A "non-transitory" computer readable medium excludes wired, wireless, optical, or other communication links that transport transitory electrical or other signals. A non-transitory computer readable medium includes media where data can be permanently stored and media where data can be stored and later overwritten, such as a rewritable optical disc or an erasable memory device.

Definitions for certain words and phrases are provided throughout this patent document, those of ordinary skill in the art should understand that in many, if not most instances, such definitions apply to prior, as well as future uses of such defined words and phrases.

BRIEF DESCRIPTION OF THE DRAWINGS

For a more complete understanding of the present disclosure and its advantages, reference is now made to the following description taken in conjunction with the accompanying drawings, in which like reference numerals represent like parts.

DETAILED DESCRIPTION

FIGS. 1 through 12C, discussed below, and the various embodiments used to describe the principles of the present disclosure in this patent document are by way of illustration only and should not be construed in any way to limit the scope of the disclosure. Those skilled in the art will understand that the principles of the present disclosure may be implemented in any suitably arranged system or device.

Figure 1:
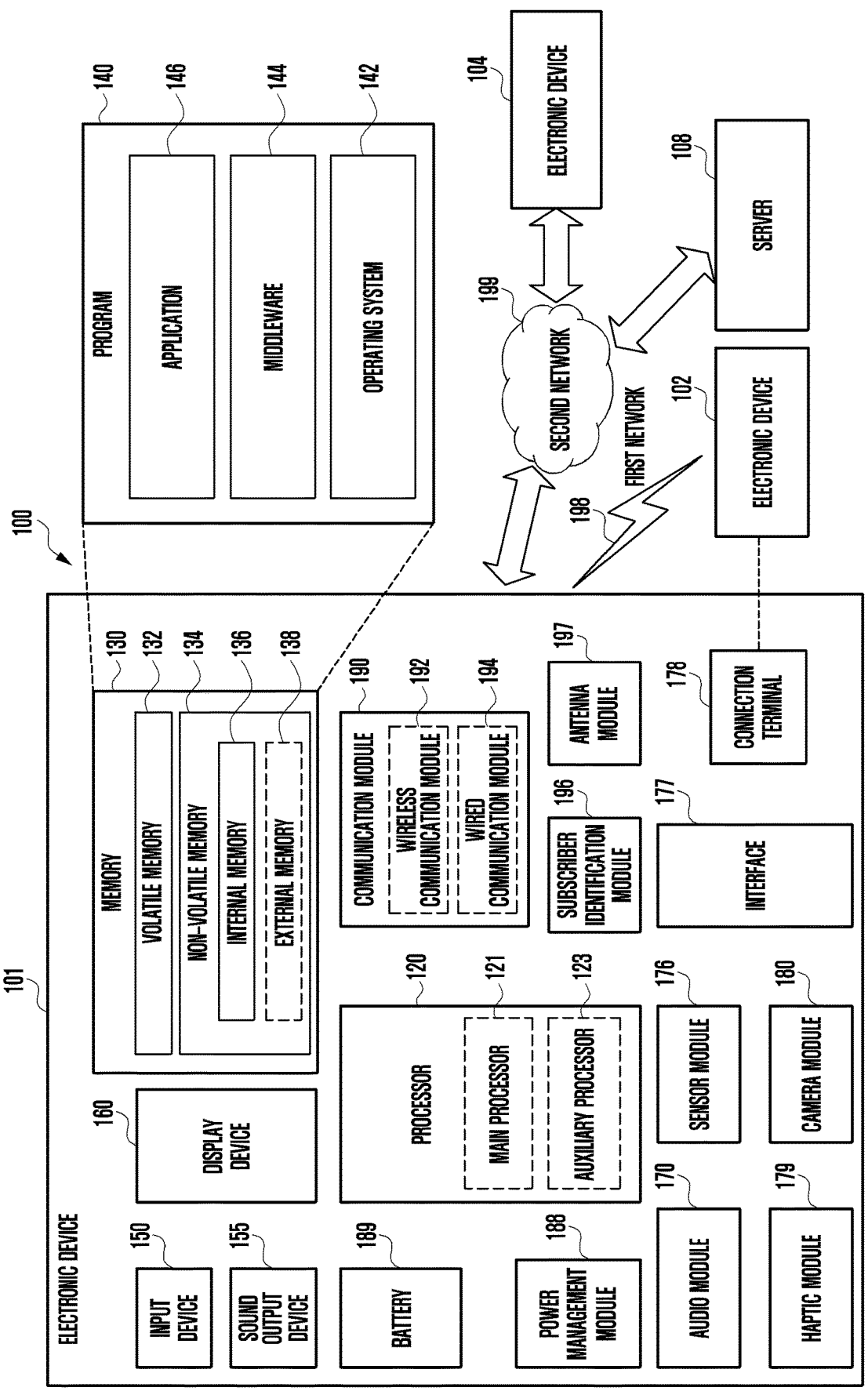
FIG. 1 is a block diagram illustrating an electronic device in a network environment according to various embodiments of the disclosure.

FIG. 1 is a block diagram illustrating an electronic device 101 in a network environment 100 according to various embodiments. Referring to FIG. 1, the electronic device 101 in the network environment 100 may communicate with an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module (SIM) 196, or an antenna module 197. In some embodiments, at least one (e.g., the display device 160 or the camera module 180) of the components may be omitted from the electronic device 101, or one or more other components may be added in the electronic device 101. In some embodiments, some of the components may be implemented as single integrated circuitry. For example, the sensor module 176 (e.g., a fingerprint sensor, an iris sensor, or an illuminance sensor) may be implemented as embedded in the display device 160 (e.g., a display).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may load a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), and an auxiliary processor 123 (e.g., a graphics processing unit (GPU), an image signal processor (ISP), a sensor hub processor, or a communication processor (CP)) that is operable independently from, or in conjunction with, the main processor 121. Additionally or alternatively, the auxiliary processor 123 may be adapted to consume less power than the main processor 121, or to be specific to a specified function. The auxiliary processor 123 may be implemented as separate from, or as part of the main processor 121.

The auxiliary processor 123 may control at least some of functions or states related to at least one component (e.g., the display device 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123.

The memory 130 may store various data used by at least one component (e.g., the processor 120 or the sensor module 176) of the electronic device 101. The various data may include, for example, software (e.g., the program 140) and input data or output data for a command related thereto. The memory 130 (e.g., DRAM, SRAM or SDRAM) may include the volatile memory 132 or the non-volatile memory 134.

The program 140 may be stored in the memory 130 as software, and may include, for example, an operating system (OS) 142, middleware 144, or an application 146 (e.g., application program).

The input device 150 may receive a command or data to be used by other component (e.g., the processor 120) of the electronic device 101, from the outside (e.g., a user) of the electronic device 101. The input device 150 may include, for example, a microphone, a mouse, or a keyboard.

The sound output device 155 may output sound signals to the outside of the electronic device 101. The sound output device 155 may include, for example, a speaker or a receiver. The speaker may be used for general purposes, such as playing multimedia or playing record, and the receiver may be used for an incoming calls. According to an embodiment, the receiver may be implemented as separate from, or as part of the speaker.

The display device 160 may visually provide information to the outside (e.g., a user) of the electronic device 101. The display device 160 may include, for example, a display, a hologram device, or a projector and control circuitry to control a corresponding one of the display, hologram device, and projector. According to an embodiment, the display device 160 may include touch circuitry adapted to detect a touch, or sensor circuitry (e.g., a pressure sensor) adapted to measure the intensity of force incurred by the touch.

The audio module 170 may convert a sound into an electrical signal and vice versa. According to an embodiment, the audio module 170 may obtain the sound via the input device 150, or output the sound via the sound output device 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector), The haptic module 179 may convert an electrical signal into a mechanical stimulus (e.g., a vibration or a movement) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device via the first network 198 (e.g., a short-range communication network, such as Bluetooth™, wireless-fidelity (Wi-Fi) direct, or infrared data association (IrDA)) or the second network 199 (e.g., a long-range communication network, such as a cellular network, the Internet, or a computer network (e.g., LAN or wide area network (WAN)). These various types of communication modules may be implemented as a single component (e.g., a single chip), or may be implemented as multi components (e.g., multi chips) separate from each other. The wireless communication module 192 may identify and authenticate the electronic device 101 in a communication network, such as the first network 198 or the second network 199, using subscriber information (e.g., international mobile subscriber identity (IMSI)) stored in the subscriber identification module 196.

The antenna module 197 may transmit or receive a signal or power to or from the outside (e.g., the external electronic device) of the electronic device 101. According to an embodiment, the antenna module 197 may include one or more antennas, and, therefrom, at least one antenna appropriate for a communication scheme used in the communication network, such as the first network 198 or the second network 199, may be selected, for example, by the communication module 190 (e.g., the wireless communication module 192). The signal or the power may then be transmitted or received between the communication module 190 and the external electronic device via the selected at least one antenna.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. Each of the electronic devices 102 and 104 may be a device of a same type as, or a different type, from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, or client-server computing technology may be used, for example.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a complier or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

Figure 2:
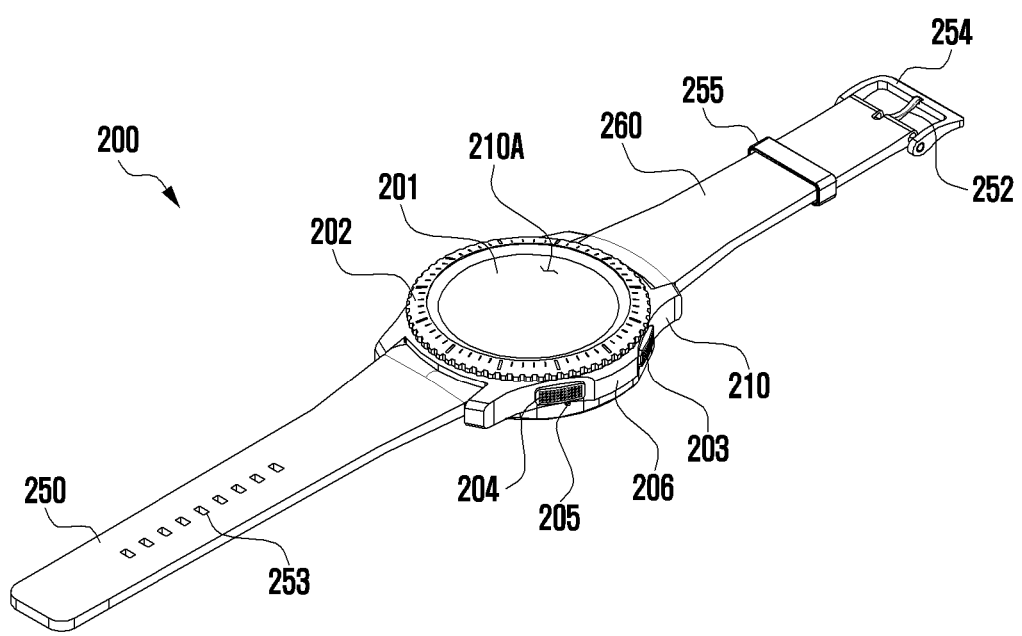
FIG. 2 is a front perspective view illustrating an electronic device according to an embodiment of the disclosure.
Figure 3:
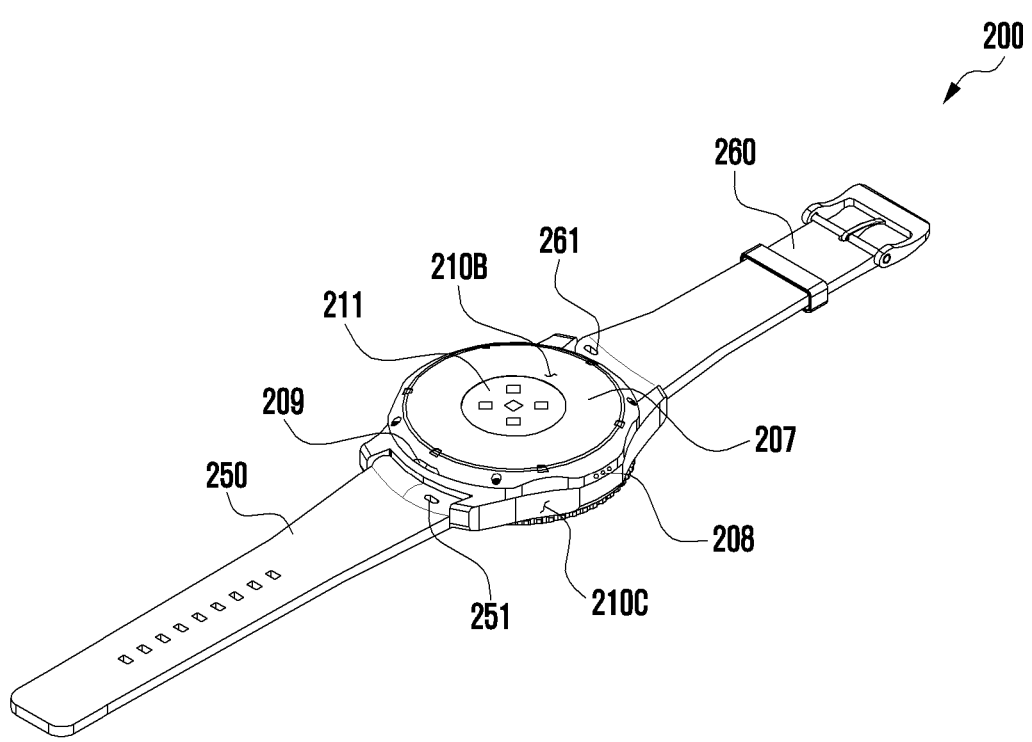
FIG. 3 is a rear perspective view illustrating the electronic device of FIG. 2 according to an embodiment of the disclosure.

FIG. 2 is a front perspective view illustrating an electronic device 200 according to an embodiment of the disclosure. FIG. 3 is a rear perspective view illustrating the electronic device 200 of FIG. 2 according to an embodiment of the disclosure.

The electronic device 200 of FIG. 2 may be at least partially similar to the electronic device 101 of FIG. 1 or may further include other components of the electronic device.

With reference FIGS. 2 and 3, the electronic device 200 (e.g., the electronic device 101 of FIG. 1) according to an embodiment may include a housing 210 including a first surface (or front surface) 210A, a second surface (or rear surface) 210B, and a side surface 210C enclosing a space between the first surface 210A and the second surface 210B, and binding members 250 and 260 connected to at least a portion of the housing 210 and configured to detachably bind the electronic device 200 to a user's body part (e.g., wrist, ankle, etc.). In another embodiment, the housing may refer to a structure forming some of the first surface 210A, the second surface 210B, and the side surfaces 210C of FIG. 2. According to one embodiment, the first surface 210A may be formed by a front plate 201 (e.g., polymer plate or glass plate including various coating layers) at least partially substantially transparent. The second surface 210B may be formed by a substantially opaque rear plate 207. The rear plate 207 may be formed by, for example, coated or colored glass, ceramic, polymer, metal (e.g., aluminum, stainless steel (STS), or magnesium), or a combination of at least two of the above materials. The side surface 210C may be formed by a side bezel structure (or "side member") 206 coupled to the front plate 201 and the rear plate 207 and including a metal and/or a polymer. In some embodiments, the rear plate 207 and the side bezel structure 206 may be integrally formed and include the same material (e.g., metal material such as aluminum). The binding members 250 and 260 may be formed with various materials and shapes. Integral and plural unit links may be formed to move each other by woven fabric, leather, rubber, urethane, metal, ceramic, or a combination of at least two of the above materials.

According to one embodiment, the electronic device 200 may include at least one of a display 220 (see FIG. 4), audio modules 205 and 208, a sensor module 211, key input devices 202, 203 and 204, and a connector hole 209. In some embodiments, the electronic device 200 may omit at least one (e.g., key input devices 202, 203, and 204, connector hole 209, or sensor module 211) of the components or may further include other components.

The display 220 may be exposed, for example, through a significant portion of the front plate 201. The display 220 may have a shape corresponding to that of the front plate 201 and have various shapes such as a circular shape, an oval shape, or a polygonal shape. The display 220 may be disposed adjacent to or to be coupled to a touch sensing circuit, a pressure sensor capable of measuring the intensity (pressure) of a touch, and/or a fingerprint sensor.

The audio modules 205 and 208 may include a microphone hole 205 and a speaker hole 208. In the microphone hole 205, a microphone for obtaining an external sound may be disposed, and in some embodiments, a plurality of microphones may be disposed to detect a direction of a sound. The speaker hole 208 may be used as an external speaker and a call receiver. In some embodiments, the speaker hole 208 and the microphone hole 205 may be implemented as one hole or a speaker (e.g., piezo speaker) may be included without the speaker hole 208.

The sensor module 211 may generate an electrical signal or a data value corresponding to an internal operating state of the electronic device 200 or an external environmental state. The sensor module 211 may include, for example, a biometric sensor module 211 (e.g., HRM sensor) disposed at the second surface 210B of the housing 210. The electronic device 200 may further include at least one of a sensor module, for example, a gesture sensor, gyro sensor, atmospheric pressure sensor, magnetic sensor, acceleration sensor, grip sensor, color sensor, infrared (IR) sensor, biometric sensor, temperature sensor, humidity sensor, or illuminance sensor.

The key input devices 202, 203, and 204 may include a wheel key 202 disposed at the first surface 210A of the housing 210 and rotatable in at least one direction and/or side key buttons 203 and 204 disposed at a side surface 210C of the housing 210. The wheel key 202 may have a shape corresponding to that of the front plate 201. In another embodiment, the electronic device 200 may not include some or all of the above-mentioned key input devices 202, 203, and 204, and the key input devices 202, 203, and 204 that are not included may be implemented into other forms such as a soft key on the display 220. The connector hole 209 may include another connector hole that may receive a connector (e.g., USB connector) for transmitting and receiving power and/or data to and from an external electronic device and a connector for transmitting and receiving audio signals to and from an external electronic device. The electronic device 200 may further include, for example, a connector cover that covers at least a portion of the connector hole 209 and that blocks a foreign material from entering the connector hole.

The binding members 250 and 260 may be detachably bound to at least a partial area of the housing 210 using locking members 251 and 261. The binding members 250 and 260 may include at least one of a fixing member 252, a fixing member fastening hole 253, a band guide member 254, or a band fixing ring 255.

The fixing member 252 may be configured to fix the housing 210 and the binding members 250 and 260 to a user's body part (e.g., wrist, ankle, etc.). The fixing member fastening hole 253 may fix the housing 210 and the binding members 250 and 260 to the user's body part to correspond to the fixing member 252. The band guide member 254 may be configured to limit the range of movement of the fixing member 252 when the fixing member 252 is fastened to the fixing member fastening hole 253; thus, the binding members 250 and 260 may be bound in close contact with the user's body part. The band fixing ring 255 may limit the range of a motion of the binding members 250 and 260 in a state in which the fixing member 252 and the fixing member fastening hole 253 are fastened.

Figure 4:
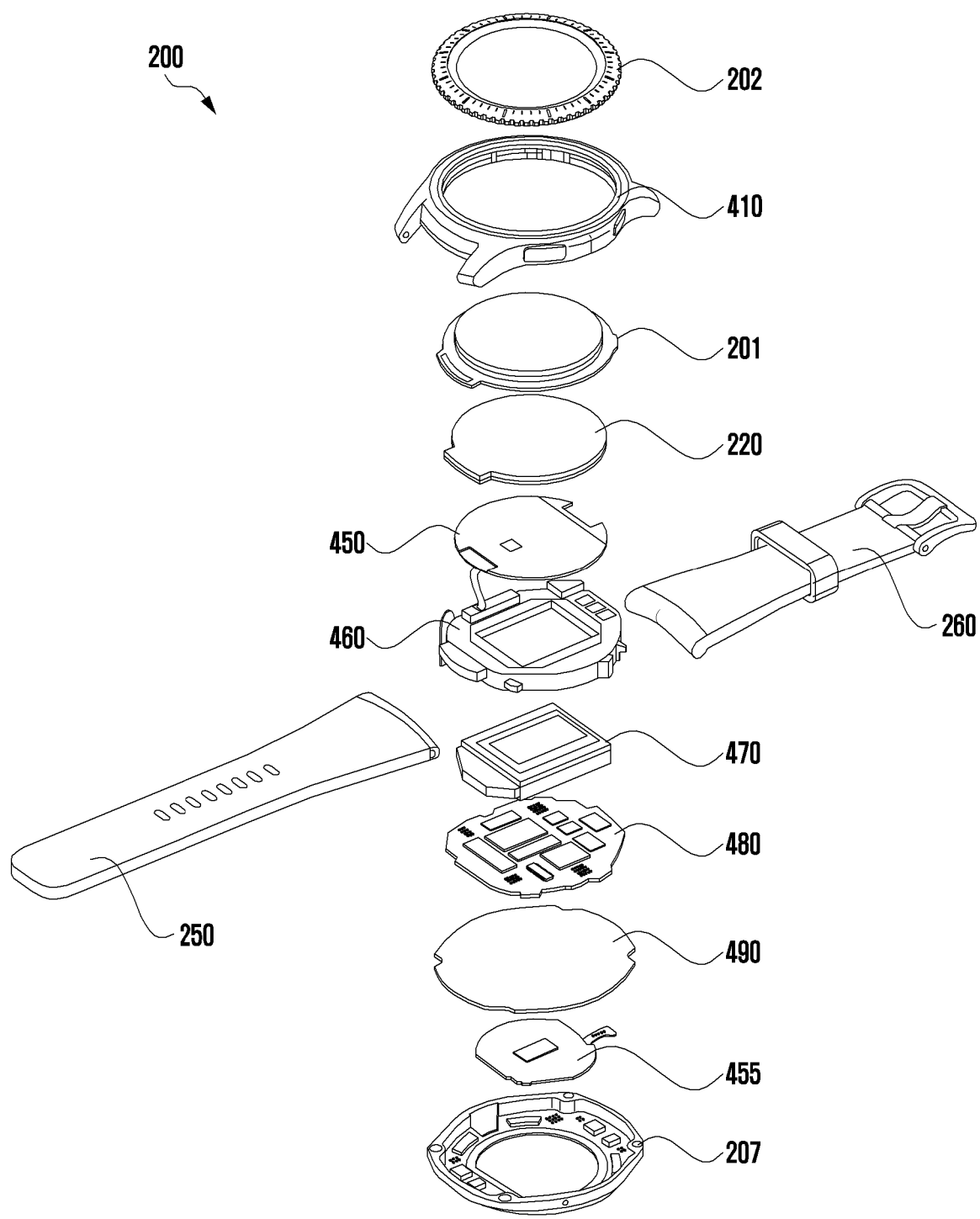
FIG. 4 is an exploded perspective view illustrating the electronic device of FIG. 2 according to an embodiment of the disclosure.

FIG. 4 is an exploded perspective view illustrating the electronic device 200 of FIG. 2 according to an embodiment of the disclosure.

With reference to FIG. 4, the electronic device 200 may include a side bezel structure 410, wheel key 202, front plate 201, display 220, first antenna 450, second antenna 455, support member 460 (e.g., bracket), battery 470, printed circuit board 480, sealing member 490, rear plate 207, and binding members 250 and 260. At least one of the components of the electronic device 400 may be the same or similar to at least one of the components of the electronic device 200 of FIG. 2 or 3, and a detailed description thereof may be omitted hereinafter.

According to an embodiment, the support member 460 may be disposed inside the electronic device 400 to be connected to the side bezel structure 410 or may be integrally formed with the side bezel structure 410. The support member 460 may be made of, for example, a metal material and/or a non-metal (e.g., polymer) material. The display 220 may be coupled to one surface of the support member 460, and the printed circuit board 480 may be coupled to the other surface of the support member 460. For example, a conductive path may be formed at least partially in the support member 460, and the conductive path may be electrically connected to the printed circuit board 480. According to an embodiment, the electronic device 400 may receive the user's biometric signal and transfer the received biometric signal to the printed circuit board 480 through a conductive path formed in the support member 460. In the printed circuit board 480, a processor (e.g., the processor 120 of FIG. 1), a memory (e.g., the memory 130 of FIG. 1), and/or an interface may be mounted. The processor may include, for example, at least one of a central processing unit (CPU), application processor (AP), graphic processing unit (GPU), sensor processor, or communication processor (CP). The memory 130 may include, for example, a volatile memory (e.g., the volatile memory 132 of FIG. 1) or a non-volatile memory (e.g., the non-volatile memory 134 of FIG. 1). The interface may include, for example, a high definition multimedia interface (HDMI), universal serial bus (USB) interface, secure digital (SD) card interface, and/or audio interface. The interface may, for example, electrically or physically connect the electronic device 400 to an external electronic device and include a USB connector, an SD card/MMC connector, or an audio connector.

The battery 470 is a device for supplying power to at least one component of the electronic device 400, and may include, for example, a non-rechargeable primary cell, a rechargeable secondary cell, or a fuel cell. At least a portion of the battery 470 may be disposed, for example, on substantially the same plane as that of the printed circuit board 480. The battery 470 may be integrally disposed inside the electronic device 400 or may be detachably disposed at the electronic device 400.

The first antenna 450 may be disposed between the display 220 and the support member 460. The first antenna 450 may include, for example, a near field communication (NFC) antenna, a wireless charging antenna, and/or a magnetic secure transmission (MST) antenna. The first antenna 450 may, for example, perform short-range communication with an external device, wirelessly transmit and receive power used for charging, and transmit a magnetic-based signal including short-range communication signals or payment data. In another embodiment, an antenna structure may be formed by a portion of the side bezel structure 410 and/or the support member 460 or a combination thereof.

The second antenna 455 may be disposed between the printed circuit board 480 and the rear plate 207. The second antenna 455 may include, for example, a near field communication (NFC) antenna, a wireless charging antenna, and/or a magnetic secure transmission (MST) antenna. The second antenna 455 may, for example, perform short-range communication with an external device, wirelessly transmit and receive power used for charging, and transmit a magnetic-based signal including a short-range communication signal or payment data. In another embodiment, the antenna structure may be formed by a portion of the side bezel structure 410 and/or the rear plate 207 or a combination thereof.

The sealing member 490 may be positioned between the side bezel structure 410 and the rear plate 207. The sealing member 490 may be configured to block moisture and foreign materials entered from the outside into a space enclosed by the side bezel structure 410 and the rear plate 207.

According to various embodiments, the electronic device 200 may include a biometric circuit (e.g., the sensor module 176 of FIG. 1) mounted in the printed circuit board 480 in an internal space and for measuring biometric information. According to an embodiment, the electronic device 200 may measure a user's biometric signal through at least one conductive portion (e.g., conductive member) disposed to be visually exposed at the outer surface. According to one embodiment, the at least one conductive portion is a sensing area and may be disposed in at least a partial area of a housing structure (e.g., the front plate 201, the rear plate 207, or the side bezel structure 410) forming an external shape of the electronic device 200. According to an embodiment, at least one conductive portion disposed at an outer surface of the electronic device 200 may be electrically connected to the biometric circuit mounted in the printed circuit board 480 through an electrical path. For example, in order to connect the conductive portion and the printed circuit board 480, the electrical path may be disposed in at least one structure (e.g., the support member 460, the front plate 201, or the side bezel structure 410) of the electronic device 200.

Figure 5:
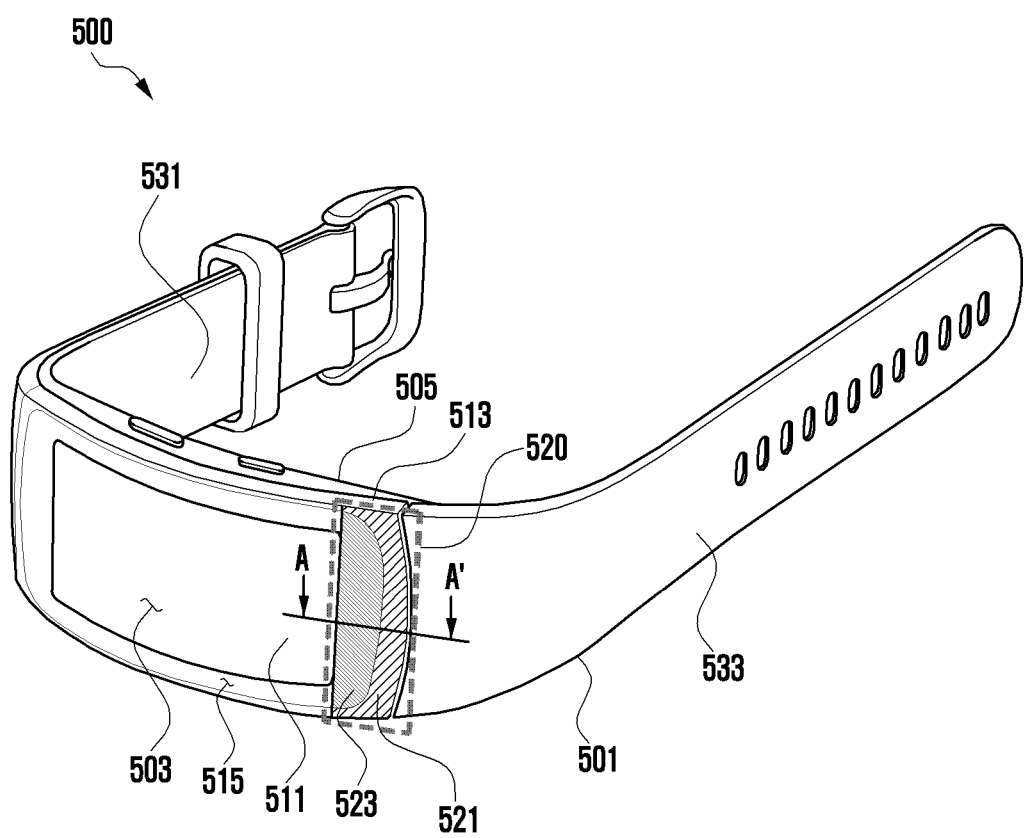
FIG. 5 is a perspective view illustrating an electronic device according to an embodiment of the disclosure.

FIG. 5 is a perspective view illustrating an electronic device 500 according to an embodiment of the disclosure.

The electronic device 500 of FIG. 5 may be at least partially similar to the electronic device 101 of FIG. 1 or the electronic device 200 of FIG. 2 or may include other components of the electronic device.

With reference to FIG. 5, the electronic device 500 may include a wearable electronic device worn on a user's wrist. According to an embodiment, the electronic device 500 may include a housing 501 (e.g., main body). According to one embodiment, the housing 501 may include a front plate 503 (e.g., the front plate 201 of FIG. 2), a rear plate 505 (e.g., the rear plate 207 of FIG. 2) facing in a direction opposite to that of the front plate 503, and/or a side bezel structure 513 (e.g., the side bezel structure 206 of FIG. 2, the side bezel structure 410 of FIG. 4) enclosing a space between the front plate 503 and the rear plate 505. According to one embodiment, the housing 501 may be formed with a conductive member (e.g., metal) or a non-conductive member (e.g., polycarbonate (PC), rubber, or urethane). In another embodiment, the housing 501 may be formed in such a manner that the conductive member is insert-injected into at least a portion of the non-conductive member. According to an embodiment, the electronic device 500 may include a display 511 disposed to be exposed through at least a partial area of the front plate 503 of the housing 501. According to an embodiment, the display 511 (e.g., the display device 160 of FIG. 1 and the display 220 of FIG. 4) may include a touch screen display. According to one embodiment, the display 511 may include a pressure-responsive touch screen display that responds to a pressure. According to an embodiment, the housing 501 may include a pair of binding members 531 and 533 (e.g., connection portion or strap) (e.g., the binding members 250 and 260 of FIG. 2). According to an embodiment, the electronic device 500 may be worn by winding on the wrist with the binding members 531 and 533 in a state in which the housing 501 is placed on the user's wrist. The electronic device 500 is a wearable electronic device, wherein the rear plate 505 and the binding members 531 and 533 may at least partially contact the user's wrist, and the electronic device 500 may obtain biometric information of the user from the contacted wrist.

According to an embodiment, the front plate 503 of the electronic device 500 may include a display 511 for displaying an image and a bezel area 515. The bezel area 515 may be partially formed in at least one of the front plate 503 or the side bezel structure 513. According to one embodiment, the front plate 503 may include a glass plate or a polymer plate including various coating layers. According to an embodiment, the front plate 503 may be a cover member that at least partially encloses the display 511 and the bezel area 515. The front plate 503 may include, for example, window glass for protecting an external impact. The window glass may at least partially protect the display 511 and the bezel area 515 from an external impact. According to an embodiment, the window glass may include a protective member formed to correspond to the size of the display 511 included in the front plate 503 or the size of the display 511 and the bezel area 515.

According to one embodiment, the rear plate 505 of the electronic device 500 may be in contact with the user's wrist, and include at least partially a conductive member (e.g., biometric sensor) so as to obtain the user's biometric information. According to one embodiment, the rear plate 505 may be a cover member at least partially enclosing the conductive member.

According to an embodiment, the electronic device 500 may include a sensing area 520. According to one embodiment, the sensing area 520 may include a first conductive portion 521 (e.g., first electrode) disposed in at least a partial area of the side bezel structure 513 or a second conductive portion 523 (e.g., second electrode) disposed in at least a partial area of the front plate 503. For example, the first conductive portion 521 and/or the second conductive portion 523 may be formed in such a manner that a conductive material is applied or deposited to at least a partial area of the side bezel structure 513 and/or the front plate 503 to be used at least partially as an electrode. According to an embodiment, the first conductive portion 521 and the second conductive portion 523 may be disposed to be adjacent to or spaced apart from each other in a state of being insulated from each other. According to another embodiment, the first conductive portion 521 may be formed at least partially in the side bezel structure 513. The second conductive portion 523 may be formed at least partially in the front plate 503. When the side bezel structure 513 and the front plate 503 are coupled, the first conductive portion 521 and the second conductive portion 523 may be disposed adjacent to each other. According to another embodiment, the first conductive portion 521 and the second conductive portion 523 may be used as one electrode or may be used as different electrodes, respectively. In another embodiment, both the first conductive portion 521 and the second conductive portion 523 may be disposed in the side bezel structure 513. In another embodiment, both the first conductive portion 521 and the second conductive portion 523 may be disposed in the front plate 503. In another embodiment, the first conductive portion 521 and/or the second conductive portion 523 may be disposed in the rear plate 505.

According to an embodiment, the processor (e.g., the processor 120 of FIG. 1) of the electronic device 500 may obtain biometric information of the user through the sensing area 520. According to an embodiment, the processor 120 of the electronic device 500 may obtain first biometric information based on the first conductive portion 521 and obtain second biometric information based on the second conductive portion 523. According to an embodiment, the processor 120 may integrate the first biometric information and the second biometric information to use the integrated biometric information as one biometric information or use each of the first biometric information and the second biometric information as different types of biometric information.

Figure 6:
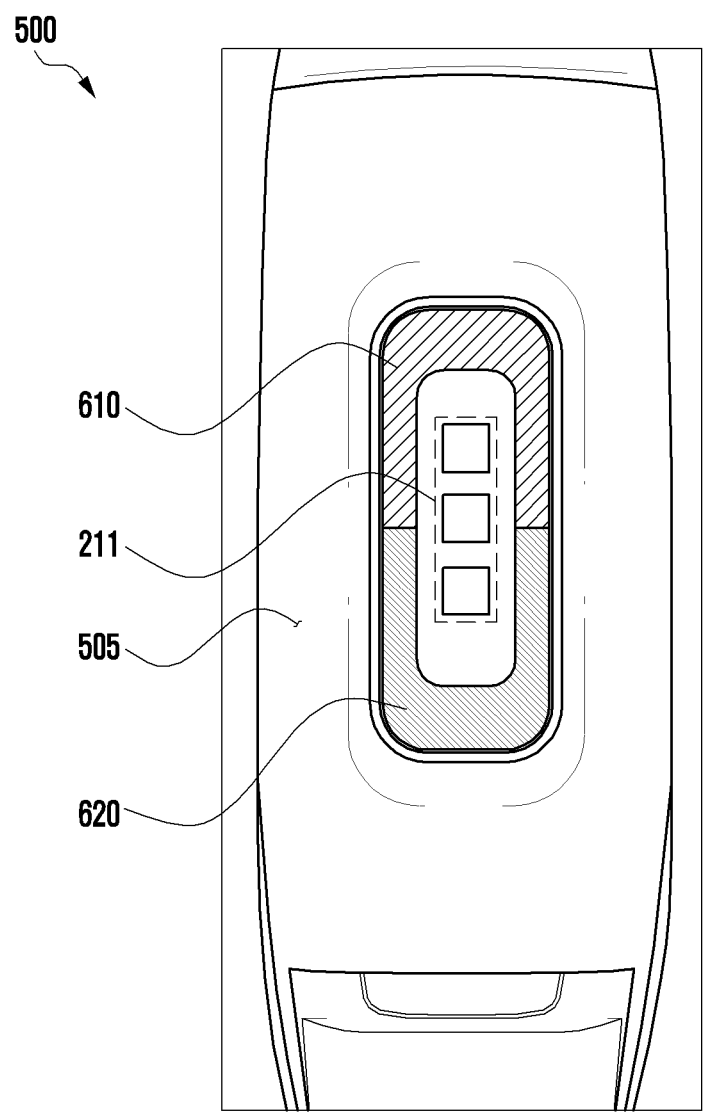
FIG. 6 is a diagram illustrating a portion of a rear surface of the electronic device of FIG. 5 according to an embodiment of the disclosure.

FIG. 6 is a diagram illustrating a portion of a rear surface of the electronic device of FIG. 5 according to an embodiment of the disclosure.

With reference to FIG. 6, the rear plate 505 (e.g., the rear plate 207 of FIG. 2) of the electronic device 500 may include a sensor module 211 (e.g., the sensor module 176 of FIG. 1) disposed to be exposed through at least a partial area. According to an embodiment, the sensor module 211 may obtain an electrical signal or a data value corresponding to an external environmental state. According to an embodiment, the sensor module 211 may include a biometric sensor (e.g., electrocardiogram (ECG) sensor or heart rate monitor (HRM) sensor). For example, the processor 120 (e.g., the processor 120 of FIG. 1) of the electronic device 500 may measure a user's heart rate using a biometric sensor.

According to an embodiment, the electronic device 500 may include a third conductive portion 610 and a fourth conductive portion 620 disposed to be exposed through at least a partial area of the rear plate 505. According to an embodiment, the electronic device 500 may obtain biometric information (e.g., electrocardiogram information) of the user based on the third conductive portion 610 and the fourth conductive portion 620. According to an embodiment, the electronic device 500 may measure the user's electrocardiogram based on at least three conductive portions (e.g., the first conductive portion 521 and the second conductive portion 523 of FIG. 5, the third conductive portion 610 or the fourth conductive portion 620 of FIG. 6). According to an embodiment, the electronic device 500 may measure the user's electrocardiogram using at least three conductive portions of the first conductive portion 521 and the second conductive portion 523 disposed at the front plate 503 and the third conductive portion 610 and the fourth conductive portion 620 disposed at the rear plate 505. For example, two of the three conductive portions may be used as electrodes having different polarities (e.g., +,−), and the other conductive portion may be used as the ground (GND). According to one embodiment, the at least one conductive portion may be integrated and used as one electrode or may be used individually as respective different electrodes. According to one embodiment, the third conductive portion 610 and/or the fourth conductive portion 620 may be implemented based on a conductive electrode member such as indium phosphide (InP), right leg drive (RLD), or indium nitride (InN).

Figure 7:
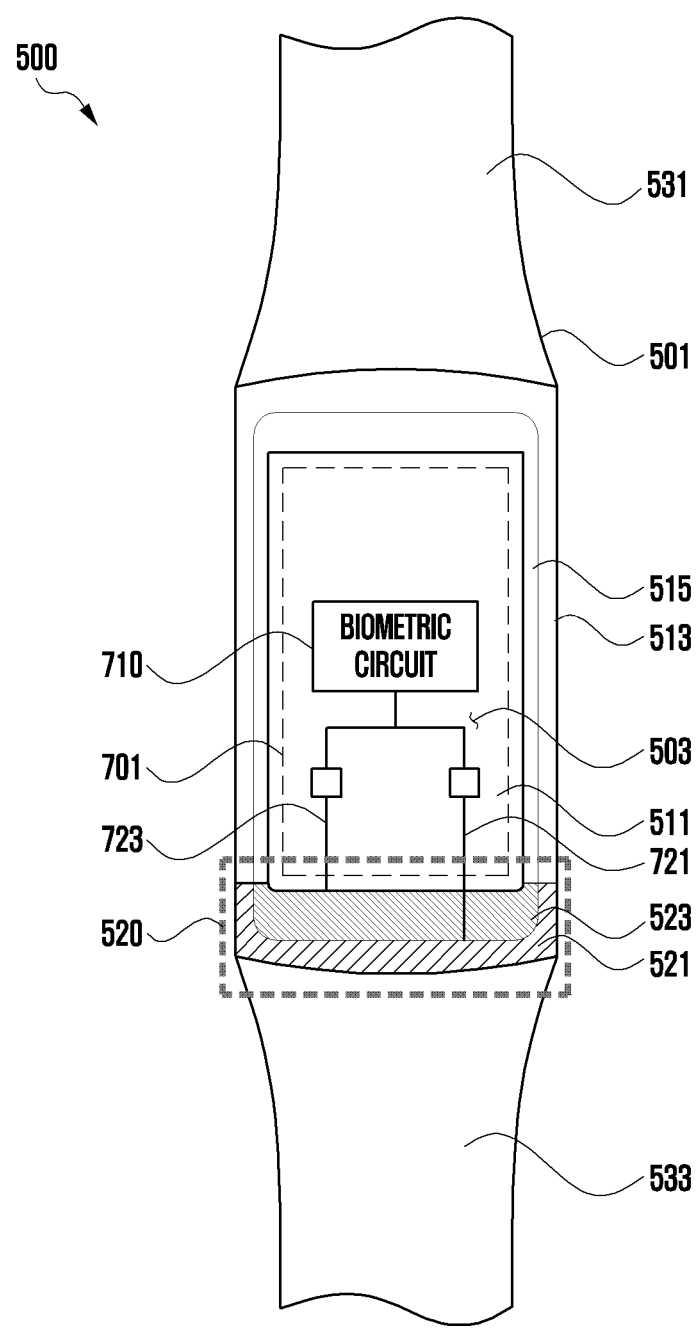
FIG. 7 is a diagram illustrating a configuration in which a first conductive portion and a second conductive portion and a biometric circuit are electrically connected in the electronic device of FIG. 5 according to an embodiment of the disclosure.

FIG. 7 is a diagram illustrating a configuration in which a first conductive portion 521 and a second conductive portion 523 and a biometric circuit 710 are electrically connected in the electronic device 500 of FIG. 5 according to an embodiment of the disclosure.

FIG. 7 is a diagram illustrating a front surface (the first surface 210A of FIG. 2) of the electronic device 500. With reference to FIG. 7, the electronic device 500 may be implemented to represent the front plate 503 at the front surface. According to an embodiment, the front plate 503 may be formed in a structure enclosed by the side bezel structure 513 and be formed such that the display 511 is at least partially exposed. According to an embodiment, a bezel area 515 may be formed between the display 511 and the side bezel structure 513. According to an embodiment, the front plate 503 may include a display 511 and a bezel area 515.

According to an embodiment, at least a partial area of the side bezel structure 513 may be implemented with the first conductive portion 521, and at least a partial area of the bezel area 515 may be implemented with the second conductive portion 523. According to another embodiment, the window glass may be disposed to cover at least a partial area of the display 511 and the bezel area 515, and at least a partial area of the window glass may be implemented with the second conductive portion 523. For example, the window glass may be formed with a transparent member, and the second conductive portion 523 may be implemented with a transparent electrode. For example, the first conductive portion 521 and the second conductive portion 523 may be used as at least one electrode and be used as at least one sensor. The first conductive portion 521 and the second conductive portion 523 may be included in at least one sensing area 520. The first conductive portion 521 and the second conductive portion 523 may be implemented to be adjacent to each other and be used as one electrode. According to an embodiment, when the first conductive portion 521 and the second conductive portion 523 are integrated and used, the sensing area 520 may be extended and a user's biometric signal may be more accurately obtained. According to one embodiment, the first conductive portion 521 and/or the second conductive portion 523 may be implemented based on a conductive electrode member such as indium phosphide (InP), right leg drive (RLD), or indium nitride (InN).

According to an embodiment, in the electronic device 500, a printed circuit board 701 (e.g., the printed circuit board 480 of FIG. 4) may be disposed in an internal space, and the printed circuit board 701 may include a biometric circuit 710 for measuring a biometric signal. The first conductive portion 521 and the second conductive portion 523 may be electrically connected to the biometric circuit 710 in order to use as at least one sensor. According to one embodiment, the first conductive portion 521 may be connected to the biometric circuit 710 based on a first path 721, and the second conductive portion 523 may be connected to the biometric circuit 710 based on a second path 723. According to one embodiment, the first path 721 and/or the second path 723 may be implemented with at least one conductive path. For example, at least one conductive path may include a movement path of an electric signal formed based on a conductive material such as a conductive film, conductive paste, conductive sheet, or laser direct structuring (LDS) pattern. According to an embodiment, the first path 721 and the second path 723 may be disposed to be adjacent to or spaced from each other in an insulated state.

Figure 8A:
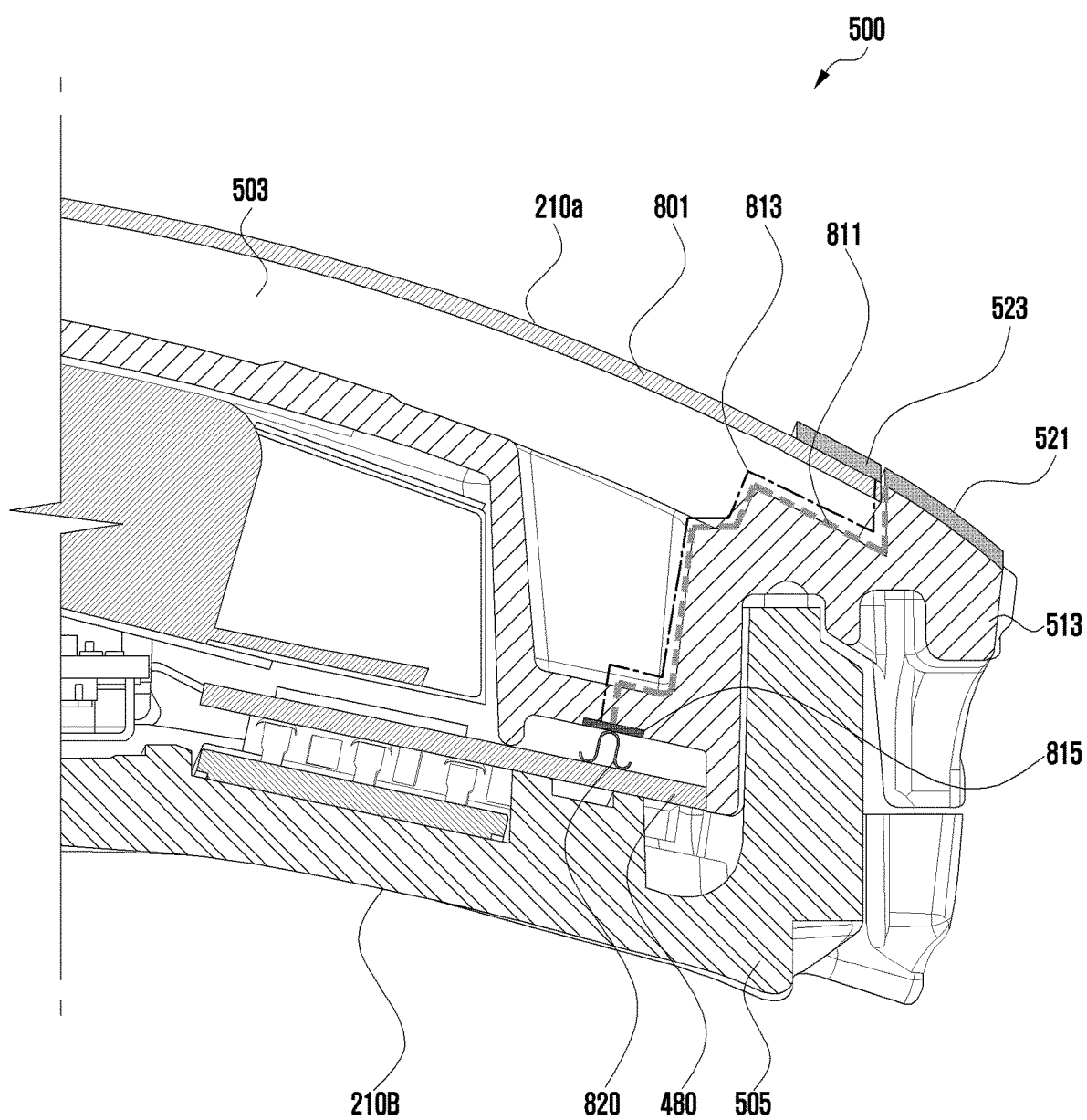
FIGS. 8A to 8B are partial cross-sectional views illustrating an electronic device taken along line A-A' of FIG. 5 according to an embodiment of the disclosure.
Figure 8B:
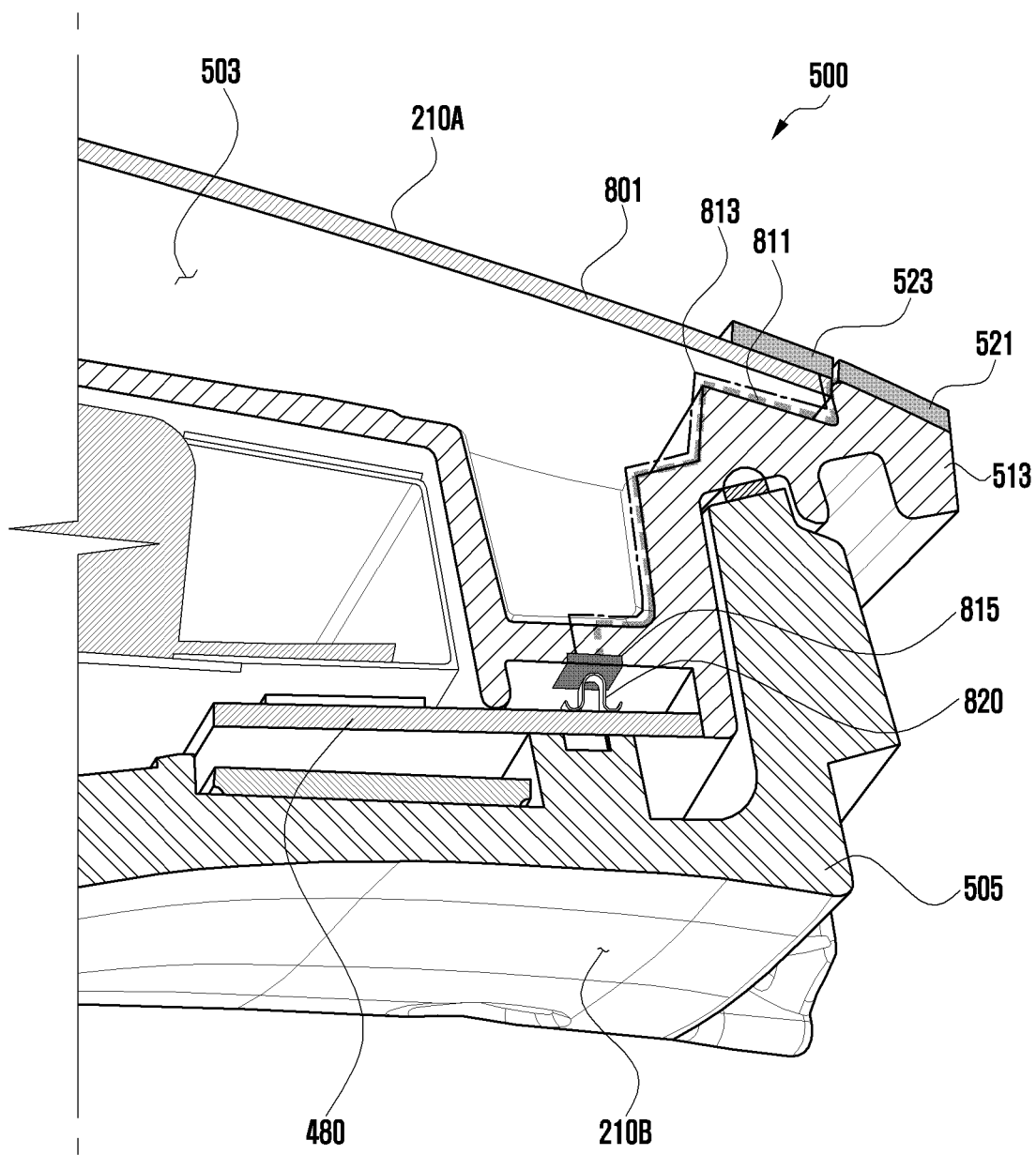

FIGS. 8A to 8B are partial cross-sectional views illustrating an electronic device taken along line A-A' of FIG. 5 according to an embodiment of the disclosure.

FIG. 8A is a partial cross-sectional view illustrating the electronic device 500 viewed vertically from line A-A', and FIG. 8B is a partial cross-sectional view illustrating the electronic device 500 viewed from another viewpoint.

With reference to FIG. 8A, the electronic device 500 may include a front plate 503, a rear plate 505 facing in a direction opposite to that of the front plate 503, and/or a side bezel structure 513 at least partially enclosing a space between the front plate 503 and the rear plate 505. According to an embodiment, the front plate 503 may be disposed to correspond to a front surface 210a of the electronic device 500, and the rear plate 505 may be disposed to correspond to a rear surface 210b of the electronic device 500. According to an embodiment, the electronic device 500 may include a display (e.g., the display 511 of FIG. 5) exposed through a significant portion of the front plate 503 and a bezel area (e.g., the bezel area 515 of FIG. 5). For example, the display included in the front plate 503 is a display device (e.g., the display device 160 of FIG. 1) of the electronic device 500 and may be a display area (e.g., active area) in which images are output. The bezel area included in the front plate 503 may include a black matrix (BM) area (e.g., an outer area of the active area) disposed at an outer edge of the display. FIG. 8B illustrates the same structure as that of FIG. 8A and is a cross-sectional view when viewed from different viewpoints.

According to an embodiment, in the electronic device 500, the first conductive portion 521 (e.g., first electrode) may be formed based on at least a partial area of the side bezel structure 513. According to an embodiment, the electronic device 500 may include window glass 801 for covering at least a partial area of the front plate 503. According to an embodiment, in the electronic device 500, a second conductive portion 523 may be formed based on at least a partial area of the window glass 801. For example, the second conductive portion 523 may be formed in a form at least partially deposited or coated based on the display and a bezel area included in the front plate 503. According to an embodiment, the first conductive portion 521 and the second conductive portion 523 may be included in at least one sensing area. According to an embodiment, the electronic device 500 may obtain a biometric signal including the user's biometric information based on the first conductive portion 521 and the second conductive portion 523. According to one embodiment, the first conductive portion 521 may be functionally connected to the printed circuit board 480 (e.g., the printed circuit board 480 of FIG. 4) through a first conductive path 811, and the second conductive portion 523 may be functionally connected to the printed circuit board 480 through a second conductive path 813. According to an embodiment, the first conductive path 811 and the second conductive path 813 may be formed with insulated from each other. According to one embodiment, an insulating member (e.g., insulating tape, insulating material, or insulating structure) may be disposed between the first conductive path 811 and the second conductive path 813; thus, the first conductive path 811 and the second conductive path 813 may be physically separated from each other. According to an embodiment, the first conductive path 811 and the second conductive path 813 may be implemented with different paths so as not to be adjacent by adjacent structures. According to an embodiment, the first conductive path 811 and the second conductive path 813 may be connected to at least one conductive pad 815, and the at least one conductive pad 815 may be electrically connected to the printed circuit board 480 through a conductive connecting member 820 (e.g., conductive pins or clips). According to an embodiment, the first conductive path 811 and the second conductive path 813 may be directly electrically connected to the printed circuit board 480. According to an embodiment, the first conductive path 811 may be formed in the form of an LDS pattern, and be partially formed to correspond to the surface of the side bezel structure 513. According to one embodiment, the second conductive path 813 may be formed with at least one of a conductive film, a conductive adhesive, or a conductive sheet and be partially formed according to the shape of the front plate 503 or the side bezel structure 513.

FIGS. 9A to 9F are diagrams illustrating an electrical connection path between at least one conductive portion and a printed circuit board according to an embodiment of the disclosure.

FIGS. 9A to 9F are diagrams illustrating the first conductive portion 521, the second conductive portion 523, the side bezel structure 513, the front plate 503, the first conductive path 811, the second conductive path 813, and/or the printed circuit board 480 illustrated in FIG. 8A.

Figure 9A:
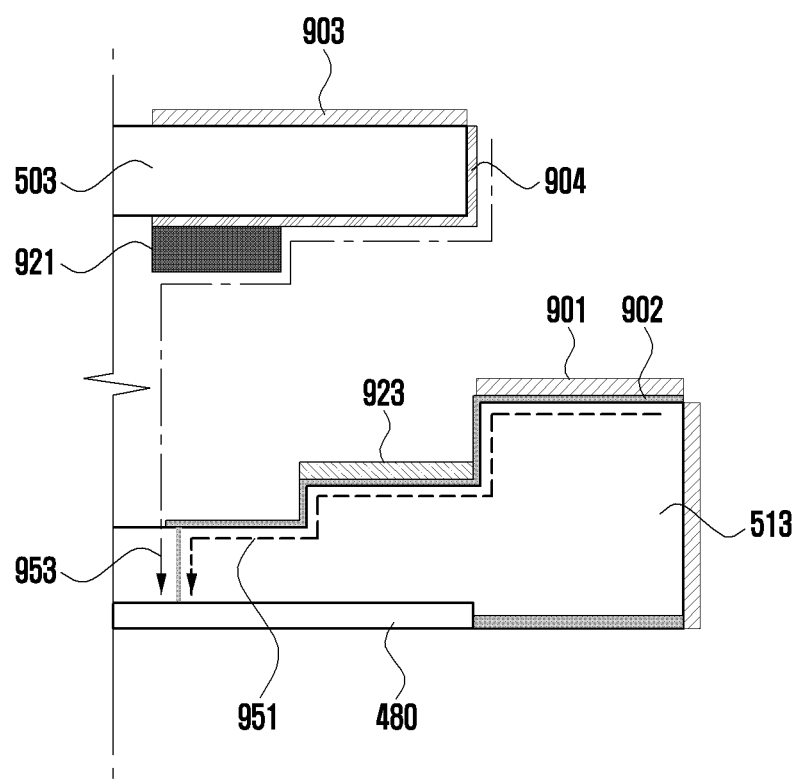
FIGS. 9A to 9F are diagrams illustrating an electrical connection path between at least one conductive portion and a printed circuit board according to an embodiment of the disclosure.

With reference to FIG. 9A, a first conductive portion 901 (e.g., the first conductive portion 521 of FIG. 8A) may be formed at least partially at one surface of the side bezel structure 513, and a second conductive portion 903 (e.g., the second conductive portion 523 of FIG. 8A) may be formed at least partially at one surface of the front plate 503. For example, the first conductive portion 901 and the second conductive portion 903 may be disposed in a form in which a conductive material is at least partially deposited or coated.

According to one embodiment, the first conductive portion 901 may be electrically connected to the printed circuit board 480 by a conductive member 902 (e.g., LDS pattern) at least partially enclosing the side bezel structure 513. According to one embodiment, the second conductive portion 903 may be electrically connected to a conductive sheet 921 by a conductive member 904 (e.g., conductive film or conductive adhesive) at least partially enclosing the front plate 503. The conductive sheet 921 may be electrically connected to a conductive member (e.g., a conductive pad 922) formed at least partially in the side bezel structure 513, and be connected to electrically to the printed circuit board 480 through the conductive member. According to an embodiment, the printed circuit board 480 may include a biometric circuit for measuring a user's biometric signal. According to an embodiment, a waterproof member 923 may be disposed to block foreign materials (e.g., moisture) entering into a space spaced between the front plate 503 and the side bezel structure 513. According to one embodiment, the first conductive portion 901 may be electrically connected to the biometric circuit of the printed circuit board 480 based on a first conductive path 951. According to an embodiment, the second conductive portion 903 may be electrically connected to the biometric circuit of the printed circuit board 480 based on a second conductive path 953.

According to an embodiment, the electronic device (e.g., the electronic device 500 of FIG. 5) may obtain a first biometric signal based on the first conductive portion 901 and obtain a second biometric signal based on the second conductive portion 903. According to an embodiment, the first biometric signal and the second biometric signal may be signals including the same biometric information. According to an embodiment, the first biometric signal and the second biometric signal may be signals including different types of biometric information.

According to an embodiment, the first conductive portion 901 and the second conductive portion 903 may be used as one sensing area for obtaining the same biometric information. According to an embodiment, the first conductive portion 901 and the second conductive portion 903 may be used as different sensing areas for obtaining different biometric information. According to an embodiment, the first conductive portion 901 may be electrically connected to the printed circuit board 480 through the first conductive path 951. According to one embodiment, the second conductive portion 903 may be electrically connected to the printed circuit board 480 through the second conductive path 953.

In FIGS. 9B to 9F, because the conductive path of the second conductive portion 903 is the same as or similar to that of FIG. 9A, a description of the second conductive portion 903 may be omitted hereinafter. FIGS. 9B to 9F variously illustrate conductive paths of the first conductive portion 901.

Figure 9B:
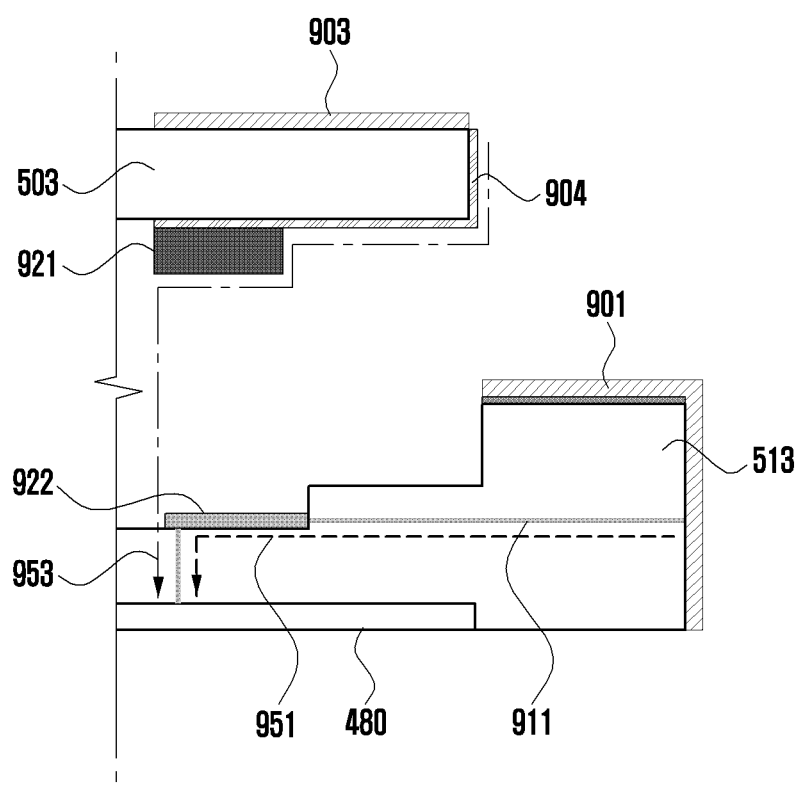

With reference to FIG. 9B, a first conductive portion 901 may be formed at least partially at one surface of the side bezel structure 513. The first conductive portion 901 may be disposed in a form in which a conductive material is deposited or coated at least partially at one surface of the side bezel structure 513. According to an embodiment, the first conductive portion 901 may be electrically connected to the printed circuit board 480 by a conductive member 911 that horizontally penetrates the side bezel structure 513. For example, the conductive member 911 may include an LDS pattern. According to an embodiment, the conductive member 911 may include a conductive material for transferring a biometric signal through a first conductive path 951. According to an embodiment, the conductive member 911 may be formed to correspond to a method of forming an antenna. According to an embodiment, the antenna forming method may include a method of forming an antenna pattern integrally with a housing by putting an antenna pattern in an injection mold or a method of forming an antenna pattern by heat-bonding an antenna pattern in the housing. According to an embodiment, the first conductive portion 901 may transfer first biometric information to the printed circuit board 480 through the first conductive path 951. According to an embodiment, the conductive pad 922 may be disposed at one surface of the side bezel structure 513, and a conductive sheet 921 and the conductive pad 922 of the front plate 503 may be electrically connected. According to an embodiment, a second conductive portion 903 may transfer second biometric information to the printed circuit board 480 through a second conductive path 953.

Figure 9C:
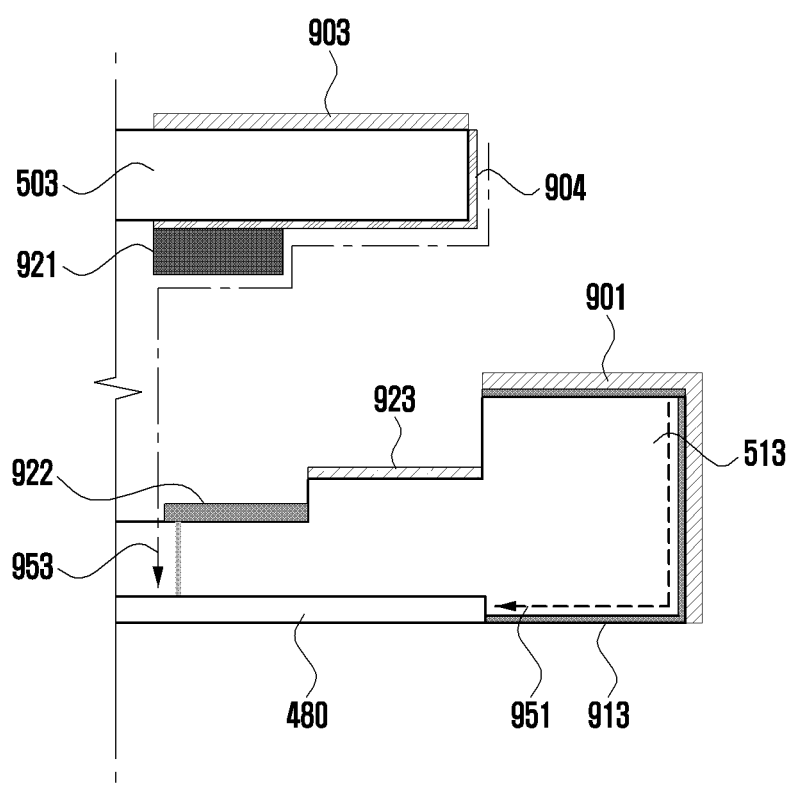

With reference to FIG. 9C, a first conductive portion 901 may be formed at least partially at one surface (e.g., upper surface) of a side bezel structure 513. As another example, a waterproof member 923 may be disposed at one surface of the side bezel structure 513. According to an embodiment, the first conductive portion 901 may be electrically connected to the printed circuit board 480 through a conductive member 913 partially disposed at a lower surface of the side bezel structure 513. For example, the conductive member 913 may include an LDS pattern.

Figure 9D:
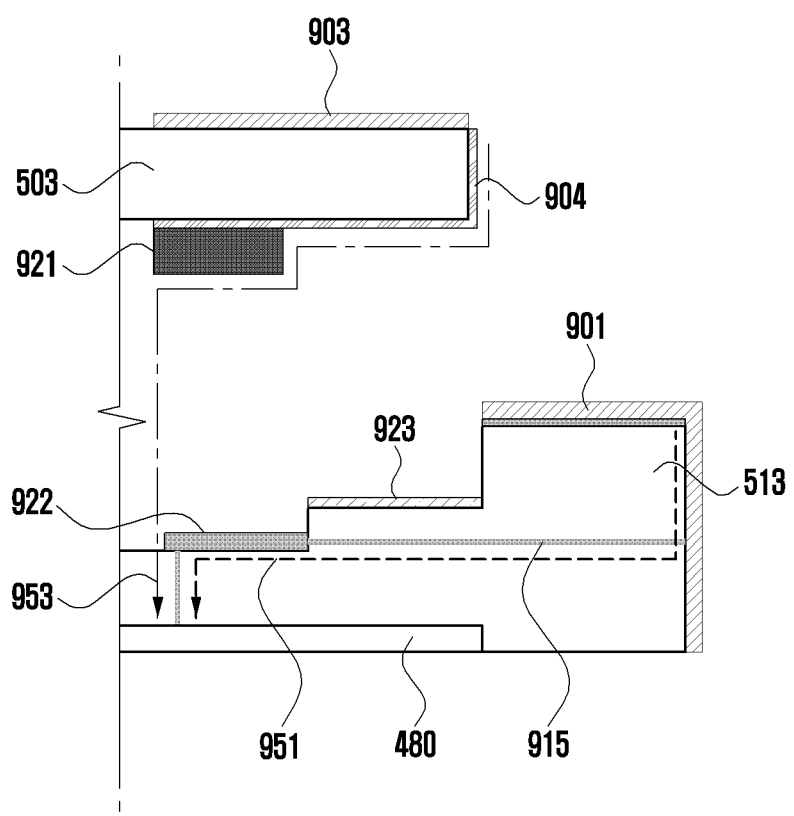

With reference to FIG. 9D, a first conductive portion 901 may be formed at least partially at one surface of a side bezel structure 513. As another example, a waterproof member 923 may be disposed at one surface of the side bezel structure 513. According to one embodiment, the first conductive portion 901 may be electrically connected to the printed circuit board 480 by a conductive member 915 that horizontally penetrates the side bezel structure 513. For example, the conductive member 915 may include an LDS pattern.

Figure 9E:
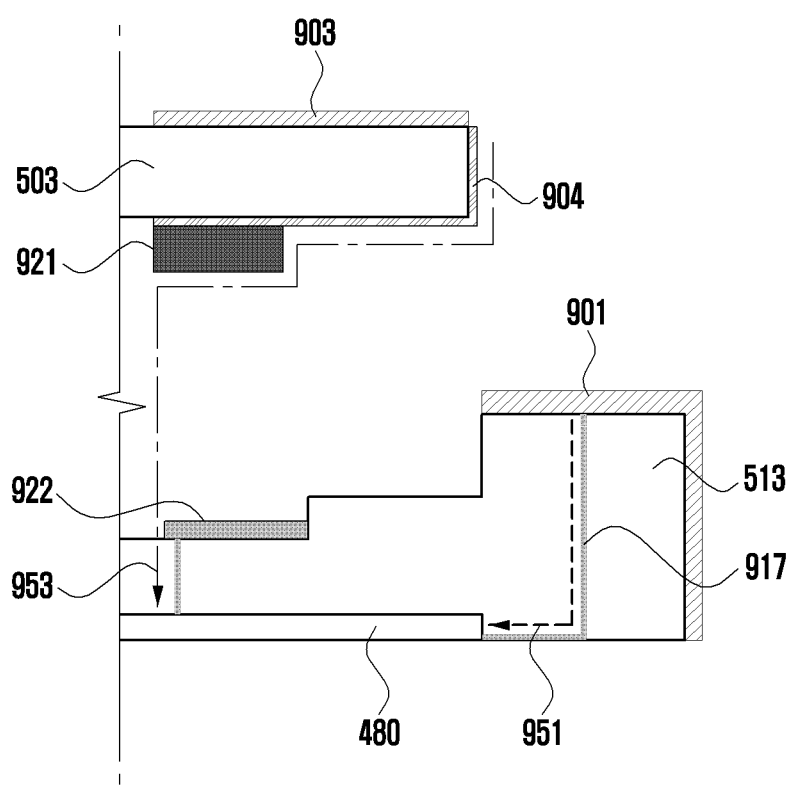

With reference to FIG. 9E, a first conductive portion 901 may be formed at least partially at one surface of a side bezel structure 513. According to an embodiment, the first conductive portion 901 may be electrically connected to the printed circuit board 480 by a conductive member 917 that vertically penetrates the side bezel structure 513. For example, the conductive member 917 may include an LDS pattern.

Figure 9F:
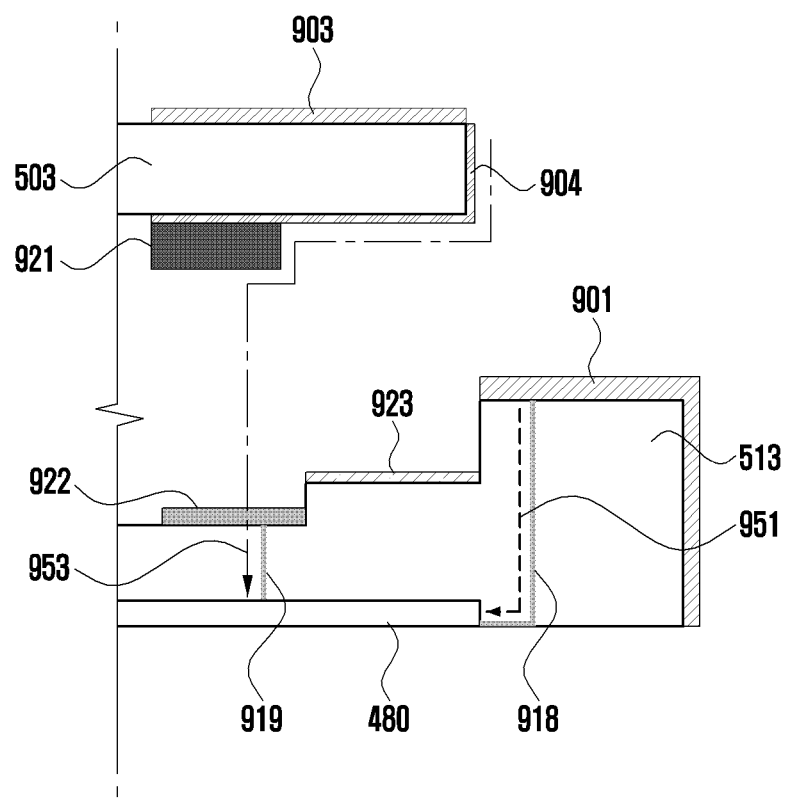

With reference to FIG. 9F, a first conductive portion 901 may be formed at least partially at one surface of a side bezel structure 513. Further, a waterproof member 923 may be disposed at one surface of the side bezel structure 513. According to one embodiment, the first conductive portion 901 may be electrically connected to the printed circuit board 480 by a conductive member 918 that vertically penetrates the side bezel structure 513. For example, the conductive member 918 may include an LDS pattern.

FIGS. 10A to 10D are diagrams illustrating a laser direct structuring (LDS) pattern corresponding to an electrical connection path between at least one conductive portion (e.g., a first conductive portion 1001 or a second conductive portion 1003) and a printed circuit board 480 according to an embodiment of the disclosure.

FIGS. 10A to 10D are diagrams illustrating the first conductive portion 521, the second conductive portion 523, the side bezel structure 513, the front plate 503, the first conductive path 811, the second conductive path 813, and/or the printed circuit board 480 illustrated in FIG. 8A.

Figure 10A:
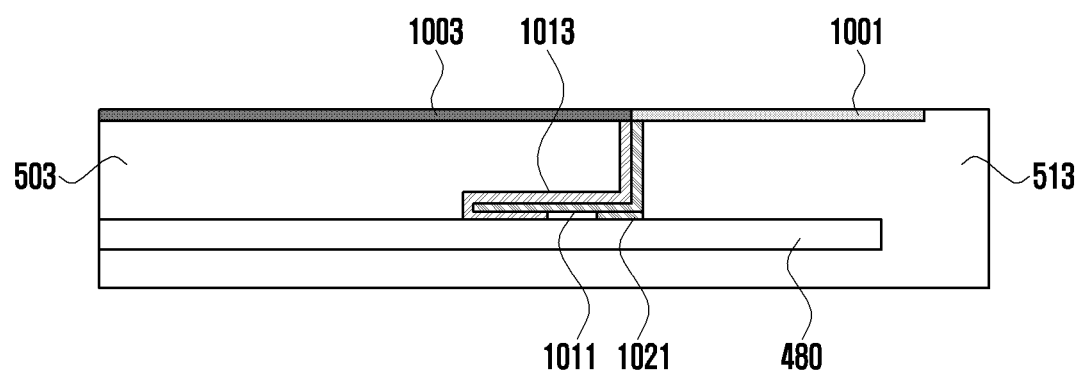
FIGS. 10A to 10D are diagrams illustrating a laser direct structuring (LDS) pattern corresponding to an electrical connection path between at least one conductive portion and a printed circuit board according to an embodiment of the disclosure.

With reference to FIG. 10A, the first conductive portion 1001 (e.g., the first conductive portion 521 of FIG. 8A) may be formed at least partially at one surface of the side bezel structure 513. The second conductive portion 1003 (e.g., the second conductive portion 523 of FIG. 8A) may be formed at least partially at one surface of the front plate 503. For example, the first conductive portion 1001 and/or the second conductive portion 1003 may be disposed in a form in which a conductive material is at least partially deposited or coated. According to one embodiment, the front plate 503 and the side bezel structure 513 may be connected by pressing.

According to one embodiment, the first conductive portion 1001 may be electrically connected to the printed circuit board 480 by a first conductive member 1011 (e.g., LDS pattern) at least partially enclosing the side bezel structure 513. According to one embodiment, the second conductive portion 1003 may be electrically connected to the printed circuit board 480 by a second conductive member 1013 (e.g., conductive film, or conductive adhesive) at least partially enclosing the front plate 503. According to an embodiment, the printed circuit board 480 may include a biometric circuit for measuring a user's biometric signal. According to an embodiment, the first conductive portion 1001 may be electrically connected to the biometric circuit of the printed circuit board 480 based on the first conductive member 1011. According to one embodiment, a conductive pad 1023 may be disposed between the first conductive member 1011 and the printed circuit board 480, and the conductive pad 1023 may function as a conductive path of the first conductive portion 1001.

According to one embodiment, the second conductive portion 1003 may be electrically connected to the biometric circuit of the printed circuit board 480 based on the second conductive member 1013. According to one embodiment, a conductive pad 1021 may be disposed between the second conductive member 1013 and the printed circuit board 480, and the conductive pad 1021 may function as a conductive path of the second conductive portion 1003.

According to an embodiment, the first conductive member 1011 may be electrically connected to the second conductive member 1013 or may be electrically connected to the printed circuit board 480 through the second conductive member 1013. For example, the first conductive member 1011 and the second conductive member 1013 may be integrated to function as one conductive member. According to another embodiment, the first conductive member 1011 and the second conductive member 1013 may not be electrically connected to each other. Each of the first conductive member 1011 and the second conductive member 1013 may be independently short-circuited.

Figure 10B:
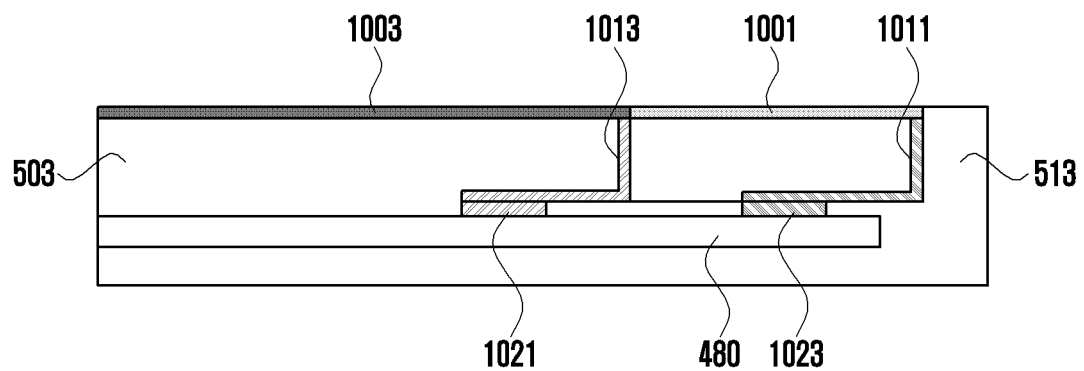
Figure 10C:
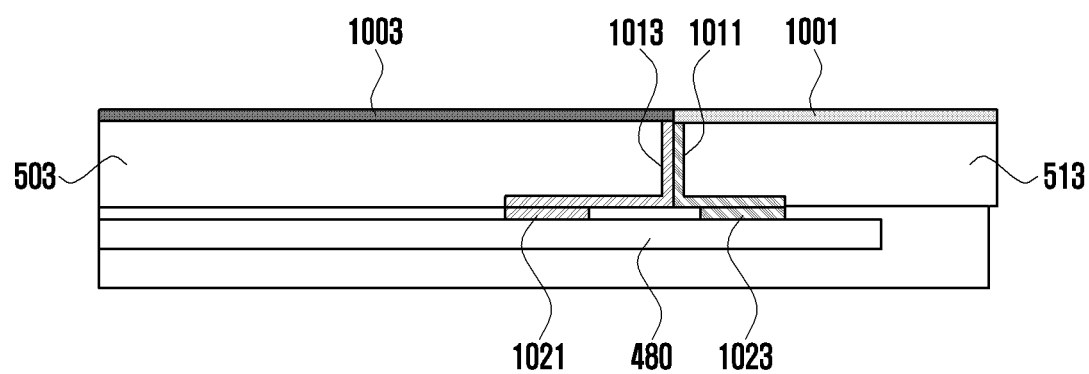
Figure 10D:
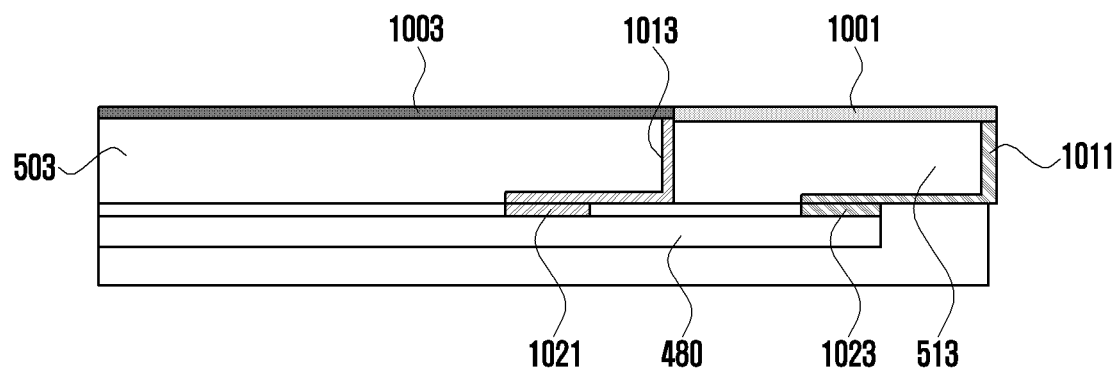

With reference FIGS. 10B to 10D, because the second conductive member 1013 of the second conductive portion 1003 is the same as or similar to that of FIG. 10A, a description of the second conductive portion 1003 may be omitted hereinafter. FIGS. 10B to 10D variously illustrate conductive paths of the first conductive portion 1001.

With reference to FIG. 10B, a first conductive portion 1001 may be formed at least partially at one surface of a side bezel structure 513. The first conductive portion 1001 may be disposed in a form in which a conductive material is at least partially deposited or coated. According to one embodiment, the first conductive portion 1001 may be electrically connected to a printed circuit board 480 by a first conductive member 1011 penetrating the inside of the side bezel structure 513. The first conductive member 1011 may include an LDS pattern that is not exposed to the outside.

With reference to FIG. 10C, a first conductive portion 1001 may be formed at least partially at one surface of a side bezel structure 513. According to one embodiment, the first conductive portion 1001 may be electrically connected to a printed circuit board 480 by a first conductive member 1011 penetrating the inside of the side bezel structure 513. The first conductive member 1011 may include an LDS pattern that is not exposed to the outside. According to one embodiment, the first conductive member 1011 and a second conductive member 1013 may be disposed in a physically separated form. According to one embodiment, the first conductive member 1011 and the second conductive member 1013 may be disposed in a short-circuit form with an insulating member disposed therebetween.

With reference to FIG. 10D, a first conductive portion 1001 may be formed at least partially at one surface of a side bezel structure 513. According to one embodiment, the first conductive portion 1001 may be electrically connected to a printed circuit board 480 by a first conductive member 1011 at least partially enclosing the outside of the side bezel structure 513. The first conductive member 1011 may include an LDS pattern. According to one embodiment, the first conductive member 1011 and the second conductive member 1013 may be disposed in a physically separated form.

According to various embodiments of the disclosure, an electronic device (e.g., the electronic device 500 of FIG. 8A) includes a housing (e.g., the housing 501 of FIG. 7) including a first cover member (e.g., the front plate 503 of FIG. 8A), a second cover member (e.g., the rear plate 505 of FIG. 8A) facing in a direction opposite to that of the first cover member 503, and a side member (e.g., the side bezel structure 513 of FIG. 8A) enclosing a space between the first cover member 503 and the second cover member 505; a support member (e.g., the support member 460 of FIG. 4) coupled to or formed integrally with the side member 513; a printed circuit board (e.g., the printed circuit board 480 of FIG. 8A) disposed in the space and including a biometric circuit (e.g., the biometric circuit 710 of FIG. 4); a first conductive portion (e.g., the first conductive portion 521 of FIG. 8A) disposed at least partially in the side member 513; a second conductive portion (e.g., the third conductive portion 610 of FIG. 6) and third conductive portion (e.g., the fourth conductive portion 620 of FIG. 6) disposed at least partially in the second cover member 505 and electrically connected to the printed circuit board 480; and/or at least one conductive path (e.g., the first conductive path 811 of FIG. 8A) disposed in the space, configured to electrically connect the biometric circuit 710 and the first conductive portion 521, and formed on the support member. The biometric circuit 710 may receive a biometric signal based on the first conductive portion 521, the second conductive portion 610, the third conductive portion 620, and the at least one conductive path 811.

According to one embodiment, the at least one conductive path 811 may include at least one of a conductive film, a conductive paste, a conductive sheet, and/or a laser direct structuring (LDS) pattern.

According to one embodiment, the biometric circuit 710 may further include an electrocardiogram (ECG) circuit, and receive a user's biometric signal based on the first conductive portion 521, the second conductive portion 610, and the third conductive portion 620, and measure the user's electrocardiogram based on the received biometric signal.

According to one embodiment, the biometric circuit 710 may receive a first biometric signal corresponding to a first polarity through the first conductive portion 521, receive a second biometric corresponding to a second polarity through one of the second conductive portion 610 and the third conductive portion 620, and measure a user's electrocardiogram based on the received first biometric signal and second biometric signal.

According to one embodiment, the first conductive portion 521 may be formed in a form deposited or coated on the side member 513.

According to one embodiment, the at least one conductive path 811 may be disposed at least partially in the housing 501 or the support member 460.

According to various embodiments of the disclosure, an electronic device (e.g., the electronic device 500 of FIG. 8A) includes a housing (e.g., the housing 501 of FIG. 7) including window glass (e.g., the window glass 801 of FIG. 8A), a first cover member (e.g., the front plate 503 of FIG. 8A) enclosing the window glass, a second cover member (e.g., the rear plate 505 of FIG. 8A) facing in a direction opposite to that of the first cover member 503, and a side member (e.g., the side bezel structure 513 of FIG. 8A) enclosing a space between the first cover member 503 and the second cover member 505; a support member (e.g., the support member 460 of FIG. 4) coupled to or formed integrally with the side member 513; a printed circuit board (e.g., the printed circuit board 480 of FIG. 8A) disposed in the space and including a biometric circuit (e.g., the biometric circuit 710 of FIG. 7); a first conductive portion (e.g., the first conductive portion 521 of FIG. 8A) formed at least partially in at least one of the first cover member 503 or the side member 513; a second conductive portion (e.g., the second conductive portion 523 of FIG. 8A) adjacent to the first conductive portion 521, at least partially formed in the window glass 801, and electrically connected to the printed circuit board 480 through a conductive member; a third conductive portion (e.g., the third conductive portion 610 of FIG. 6) and fourth conductive portion (e.g., the fourth conductive portion 620 of FIG. 6) disposed at least partially in the second cover member 505 and electrically connected to the printed circuit board 480; and/or a first conductive path (e.g., the first conductive path 811 of FIG. 8A) disposed in the space and configured to electrically connect the biometric circuit 710 and the first conductive portion 521 and a second conductive path (e.g., the second conductive path 813 of FIG. 8A) formed on the support member to electrically connect the biometric circuit 710 and the second conductive portion 523. According to one embodiment, the biometric circuit 710 receives a biometric signal based on the first conductive portion 521, the second conductive portion 523, the third conductive portion 610, the fourth conductive portion 620, the first conductive path 811, and the second conductive path 813.

According to one embodiment, the first conductive path 811 may include a conductive film, a conductive paste, and a conductive sheet, and the second conductive path may include a laser direct structuring (LDS) pattern.

According to one embodiment, the biometric circuit 710 may further include an electrocardiogram (ECG) circuit, and receive a user's biometric signal based on the first conductive portion 521, the second conductive portion 523, the third conductive portion 610, and the fourth conductive portion 620 and measure the user's electrocardiogram based on the received biometric signal.

According to one embodiment, the biometric circuit 710 may receive a first biometric signal corresponding to a first polarity through at least one of the first conductive portion 521 and the second conductive portion 523, receive a second biometric signal corresponding to a second polarity through one of the third conductive portion 610 and the fourth conductive portion 620, and measure a user's electrocardiogram based on the received first biometric signal and second biometric signal.

According to one embodiment, the first conductive portion 521 and the second conductive portion 523 may be integrated to receive together the first biometric signal corresponding to the first polarity.

According to one embodiment, an insulating member may be disposed between the first conductive path 811 and the second conductive path 813, and the first conductive path 811 and the second conductive path 813 may be separately formed by the insulating member.

According to one embodiment, the first conductive portion 521 may be formed to be at least partially deposited or coated on the window glass, and the second conductive portion 523 may be formed to be at least partially deposited or coated on at least one of the first cover member 503 or the side member 513.

FIGS. 11A to 11J are diagrams illustrating a first embodiment of implementing a first conductive portion 1104 and a second conductive portion 1105 based on a button 1110 of an electronic device 500 according to an embodiment of the disclosure.

Figure 11A:
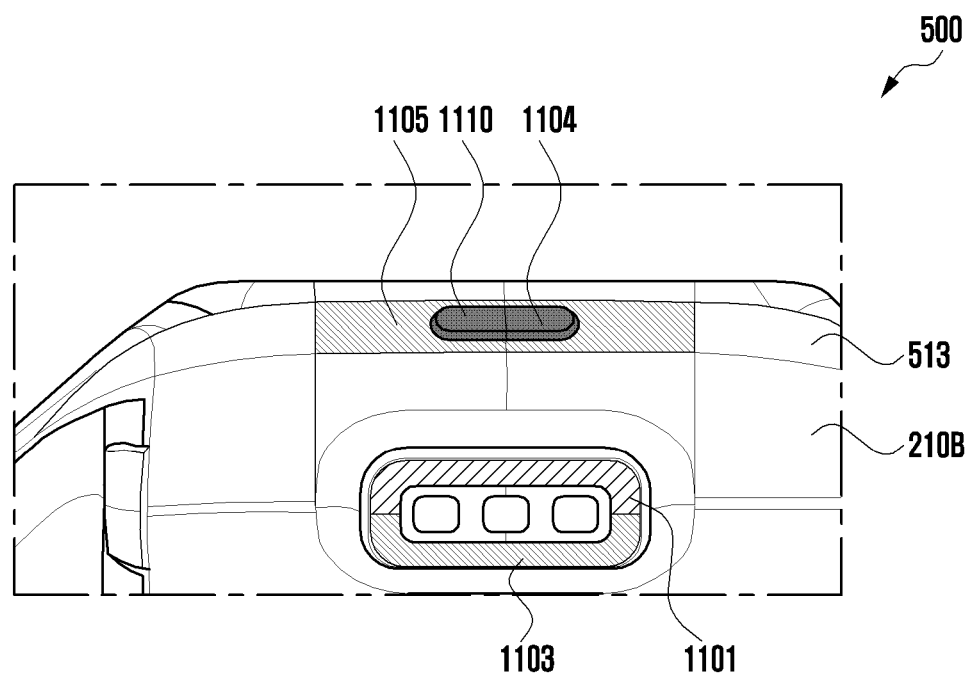
FIGS. 11A to 11J are diagrams illustrating a first embodiment of implementing a first conductive portion and a second conductive portion based on a button of an electronic device according to an embodiment of the disclosure.

FIG. 11A illustrates a first embodiment of dividing a button 1110 of the electronic device 500 and a peripheral area of the button to use the button 1110 of the electronic device 500 and the peripheral area as a first conductive portion 1104 and a second conductive portion 1105.

FIG. 11A partially illustrates a rear surface 210B and a side bezel structure 513 of the electronic device 500. According to an embodiment, the electronic device 500 may include at least one button 1110. For example, the at least one button 1110 may be at least partially disposed at the side bezel structure 513 of the electronic device 500. According to one embodiment, a position in which the at least one button 1110 is disposed is not limited to the side bezel structure 513.

With reference to FIG. 11A, the electronic device 500 may include at least one button 1110 disposed to be exposed from an internal space to the outside through at least a portion of the side bezel structure 513. According to an embodiment, the electronic device 500 may include a first conductive portion 1104 disposed through at least a portion of the button 1110 and a second conductive portion 1105 disposed in the side bezel structure 513 around the button. For example, the first conductive portion 1104 may be disposed in a form at least partially deposited or coated on at least one button 1110. The second conductive portion 1105 may be disposed in a form at least partially deposited or coated on the side bezel structure 513. According to an embodiment, the electronic device 500 may integrate and use at least one button 1110 and a peripheral area as one electrode. For example, the first conductive portion 1104 and the second conductive portion 1105 may be integrated and formed as one conductive portion (e.g., one electrode). According to an embodiment, the electronic device 500 may divide and use at least one button 1110 and a peripheral area into different electrodes. For example, the first conductive portion 1104 and the second conductive portion 1105 may be insulated from each other and be used as different conductive portions.

With reference to FIG. 11A, at least one conductive portion (e.g., a third conductive portion 1101 or a fourth conductive portion 1103) may be disposed at the rear surface 210b of the electronic device 500. According to one embodiment, the electronic device 500 may measure the user's electrocardiogram based on at least three conductive portions. For example, two of the three conductive portions may be used as different electrodes (e.g., +,-), and the remaining one conductive portion may be used as the ground (GND). According to an embodiment, when at least one of the first conductive portion 1104 and the second conductive portion 1105 is used as a positive (+) electrode, at least one of the third conductive portion 1101 and the fourth conductive portion 1103 may be used as an a negative (-) electrode. The remaining conductive portion that is not used as the positive (+) electrode or the negative (-) electrode may be used as the ground (GND).

Figure 11B:
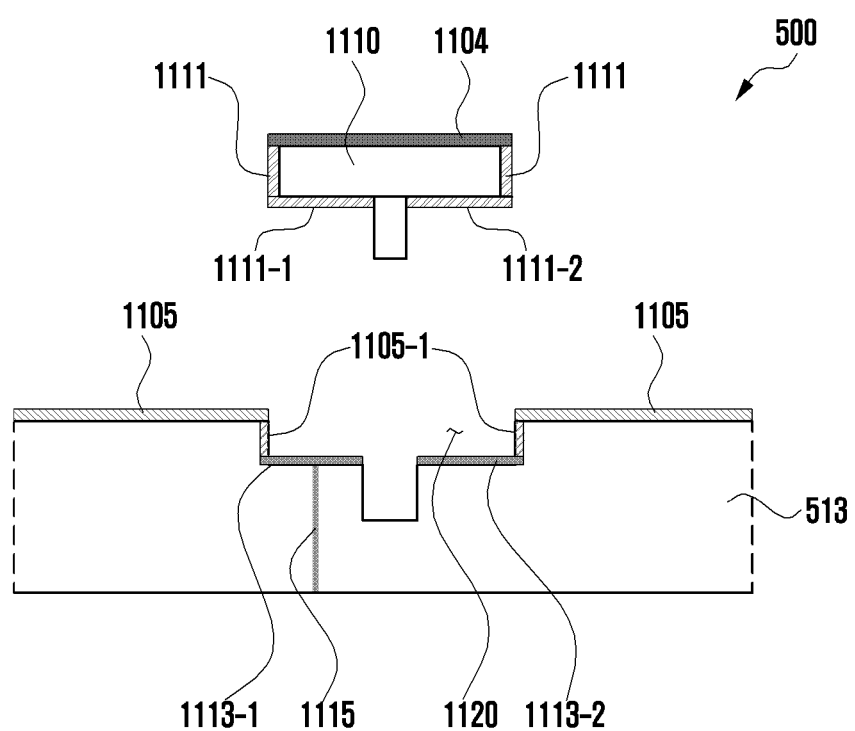

FIG. 11B illustrates a structure in which at least one button 1110 is disposed in the side bezel structure 513. According to one embodiment, the at least one button 1110 may be disposed in a form at least partially coupled to the side bezel structure 513. For example, the side bezel structure 513 may include an opening 1120, and at least one button 1110 may be coupled to the side bezel structure 513 to correspond to the opening 1120. According to an embodiment, a first conductive portion 1104 may be disposed to correspond to some areas exposed from the at least one button 1110 to the outside, and a second conductive portion 1105 may be disposed to correspond to some areas exposed from the side bezel structure 513 to the outside. The first conductive portion 1104 and the second conductive portion 1105 may be disposed adjacent to each other, but a gap may be formed between the first conductive portion 1104 and the second conductive portion 1105; thus, the first conductive portion 1104 and the second conductive portion 1105 may not be electrically coupled. According to an embodiment, the at least one button 1110 may be moved flexibly by a user input. In order to flexibly move the at least one button 1110, a gap may be formed between the at least one button 1110 and the side bezel structure 513. According to one embodiment, the first conductive portion 1104 and the second conductive portion 1105 may be electrically connected to at least one conductive member, and be electrically connected to the printed circuit board through the at least one conductive member.

According to one embodiment, the first conductive portion 1104 may be electrically connected to the printed circuit board based on a conductive member 1111 that at least partially encloses at least one button 1110, conductive pads 1113-1 and 1113-2 electrically connected to the conductive member 1111, and/or the first conductive path 1115. According to one embodiment, the second conductive portion 1105 may be electrically connected to the printed circuit board based on a conductive member 1105-1 disposed at least partially in the opening 1120 formed in the side bezel structure 513, the conductive pads 1113-1 and 1113-2 electrically connected to the conductive member 1105-1, and/or the first conductive path 1115. For example, the conductive member 1105-1 formed at least partially in the side bezel structure 513 may have one end connected to the second conductive portion 1105 and the other end connected to the conductive pads 1113-1 and 1113-2. The conductive member 1105-1 according to an embodiment may include an LDS pattern and function as a conductive path of the second conductive portion 1105. According to one embodiment, the second conductive portion 1105 may be electrically connected to the printed circuit board using an LDS pattern.

Figure 11C:
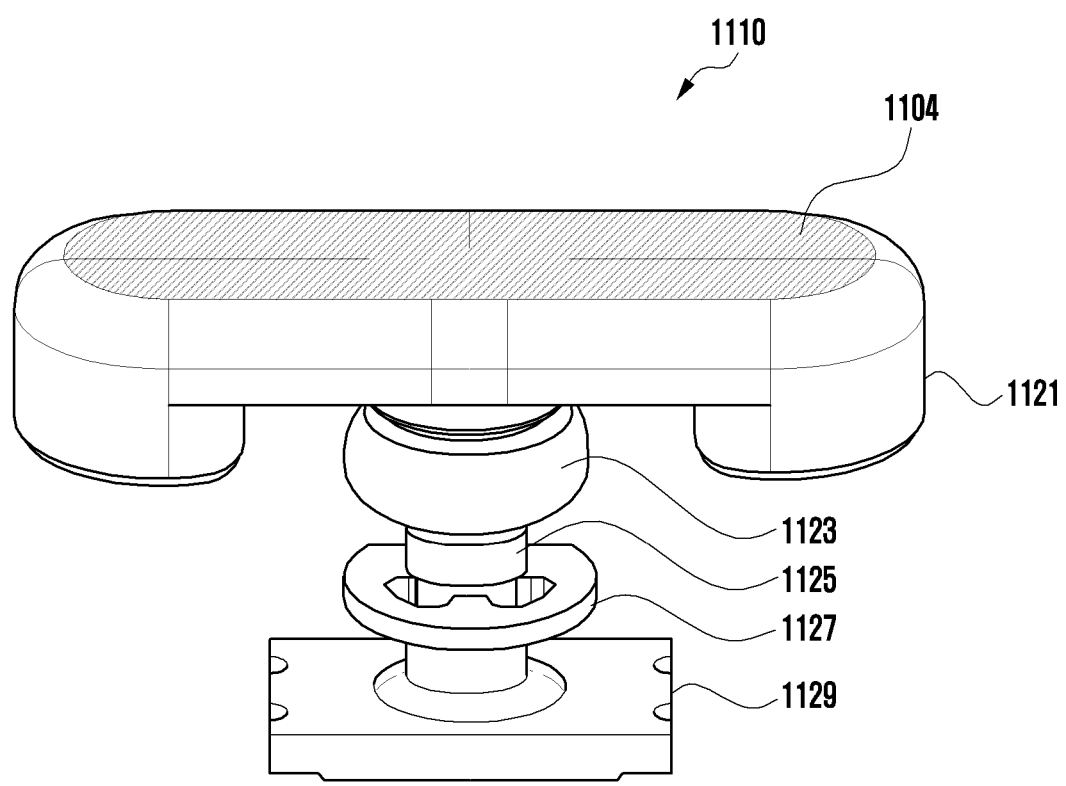

FIG. 11C illustrates a stacked state of at least one button 1110. With reference to FIG. 11C, at least one button 1110 may include a key 1121 in which a conductive member is at least partially formed, a waterproof O-ring 1123 (e.g., O-ring type waterproof member) for preventing the inflow of water, a spring member 1125, a support member 1127 for supporting at least one button 1110, and/or a dome key flexible printed circuit board (FPCB) 1129. According to an embodiment, in the at least one button 1110, a conductive material 1104 (e.g., a first conductive portion 1104) or a conductive pattern may be formed to correspond to an area exposed to the outside. For example, the conductive material 1104 may be used as one electrode. According to one embodiment, a conductive path may be included at least partially in the outer surface of the key 1121, and the conductive material 1104 may be electrically connected to the dome key FPCB 1129 through the conductive path. According to an embodiment, at least one button 1110 may obtain a biometric signal based on the conductive material 1104 and transfer the biometric signal to the dome key FPCB 1129 through the conductive path.

According to an embodiment, the at least one button 1110 may be made of a conductive material, or a conductive member may be deposited/coated on a non-conductive material. According to an embodiment, the at least one button 1110 may be at least partially coupled to the side bezel structure 513 of the electronic device 500.

Figure 11D:
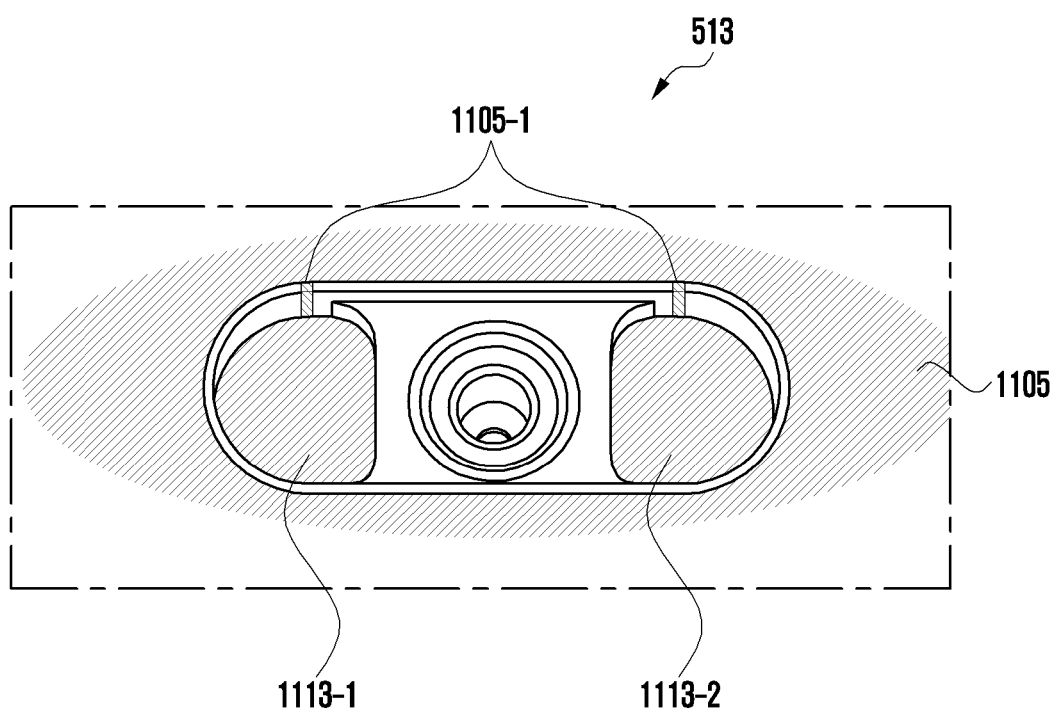

FIG. 11D illustrates a coupling area to which at least one button 1110 is coupled in the side bezel structure 513. With reference to FIG. 11D, a coupling area of the side bezel structure 513 may be formed to correspond to the shape of the at least one button 1110 so that at least one button 1110 is coupled. A conductive material 1105 (e.g., a second conductive portion 1105) may be deposited or coated at least partially at the surface of the side bezel structure 513. For example, the conductive material 1105 may be used as one electrode. According to one embodiment, the side bezel structure 513 may include a conductive member 1105-1 used as a path for transferring a biometric signal and conductive pads 1113-1 and 1113-2 electrically connected to the printed circuit board. According to an embodiment, the side bezel structure 513 may receive a biometric signal through the conductive material 1105 and transfer the received biometric signal to a printed circuit board using the conductive member 1105-1 and the conductive pads 1113-1 and 1113-2 as a transmission path. According to one embodiment, when at least one button 1110 is coupled to the side bezel structure 513, the conductive member formed in the at least one button 1110 may be electrically connected to the conductive pads 1113-1 and 1113-2.

Figure 11E:
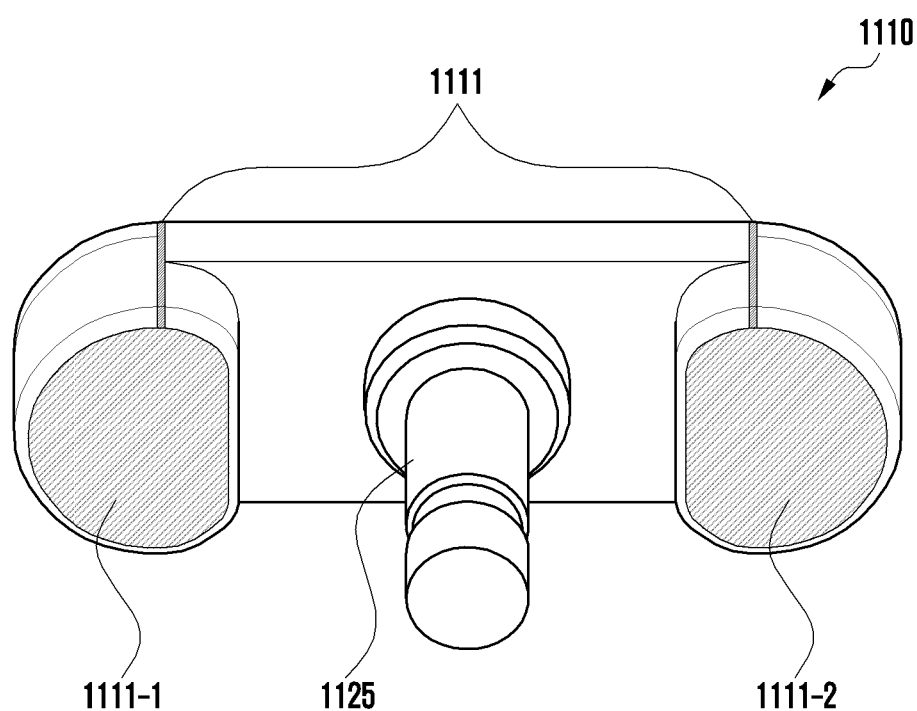

FIG. 11E illustrates a lower surface of at least one button 1110. An upper surface of the at least one button 1110 may be a surface of a first direction exposed to the outside, and a lower surface of the at least one button 1110 may be a surface of a second direction coupled to the side bezel structure 513 to be not exposed to the outside. The second direction may be opposite to the first direction.

With reference to FIG. 11E, at least one button 1110 may include conductive members 1111, 1111-1, and 1111-2 disposed at least partially at a lower surface. According to an embodiment, the conductive members 1111, 1111-1, and 1111-2 may be formed in a deposited or coated form. A conductive material (e.g., the conductive material 1104 of FIG. 11C) may be formed at an upper surface of at least one button 1110, and the conductive material may be electrically connected to the printed circuit board through the conductive members 1111, 1111-1, and 1111-2. According to an embodiment, the at least one button 1110 may be coupled to the side bezel structure 513 of the electronic device 500 using a spring member 1125. According to an embodiment, the at least one button 1110 may further include a waterproof O-ring (e.g., the waterproof O-ring 1123 of FIG. 11C) for preventing the inflow of water and a support member (e.g., the support member 1127 of FIG. 11C) for supporting the at least one button 1110.

Figure 11F:
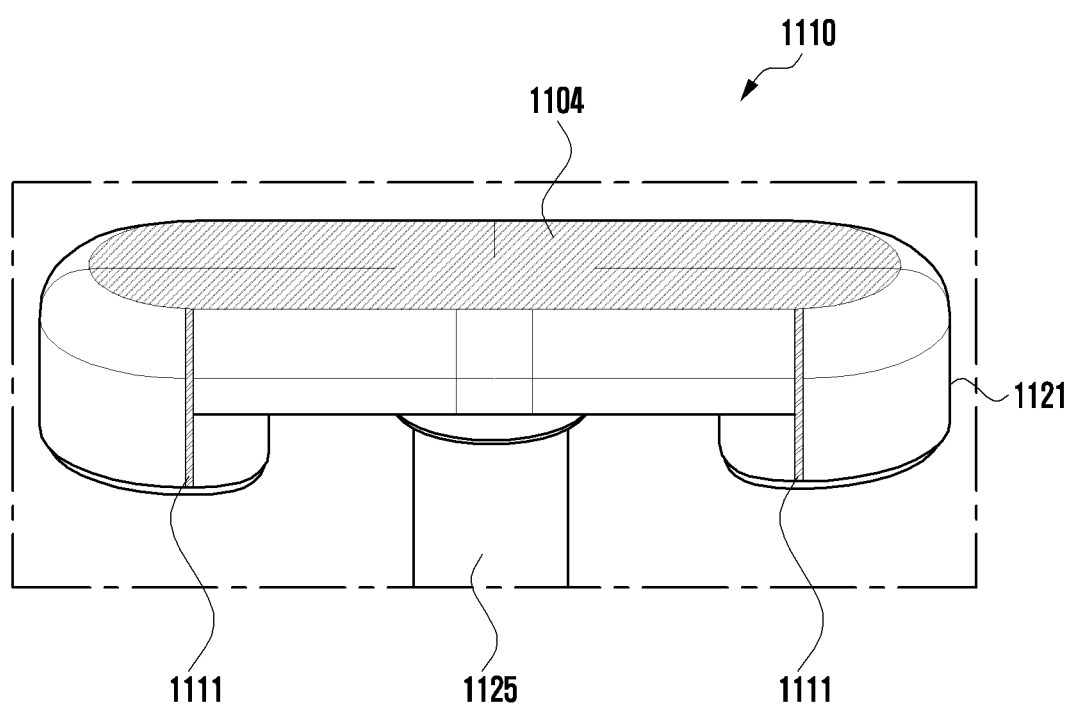

FIG. 11F partially illustrates an upper surface of at least one button 1110. The upper surface of the at least one button 1110 may be a surface exposed to the outside, and a conductive material (e.g., the conductive material 1104 of FIG. 11C) may be at least partially formed at the upper surface thereof. For example, the conductive material 1104 may be formed in a form deposited or coated on at least one button 1110. According to an embodiment, when the user's body part contacts the conductive material 1104, at least one button 1110 may receive the user's bio signal. The biometric signal may be transferred to a printed circuit board based on the conductive material 1104 and the conductive member 1111. The spring member 1125 may be formed at a lower surface of the at least one button 1110 and be at least partially coupled to a side bezel structure (e.g., the side bezel structure 513 of FIG. 11D) through the spring member 1125.

Figure 11G:
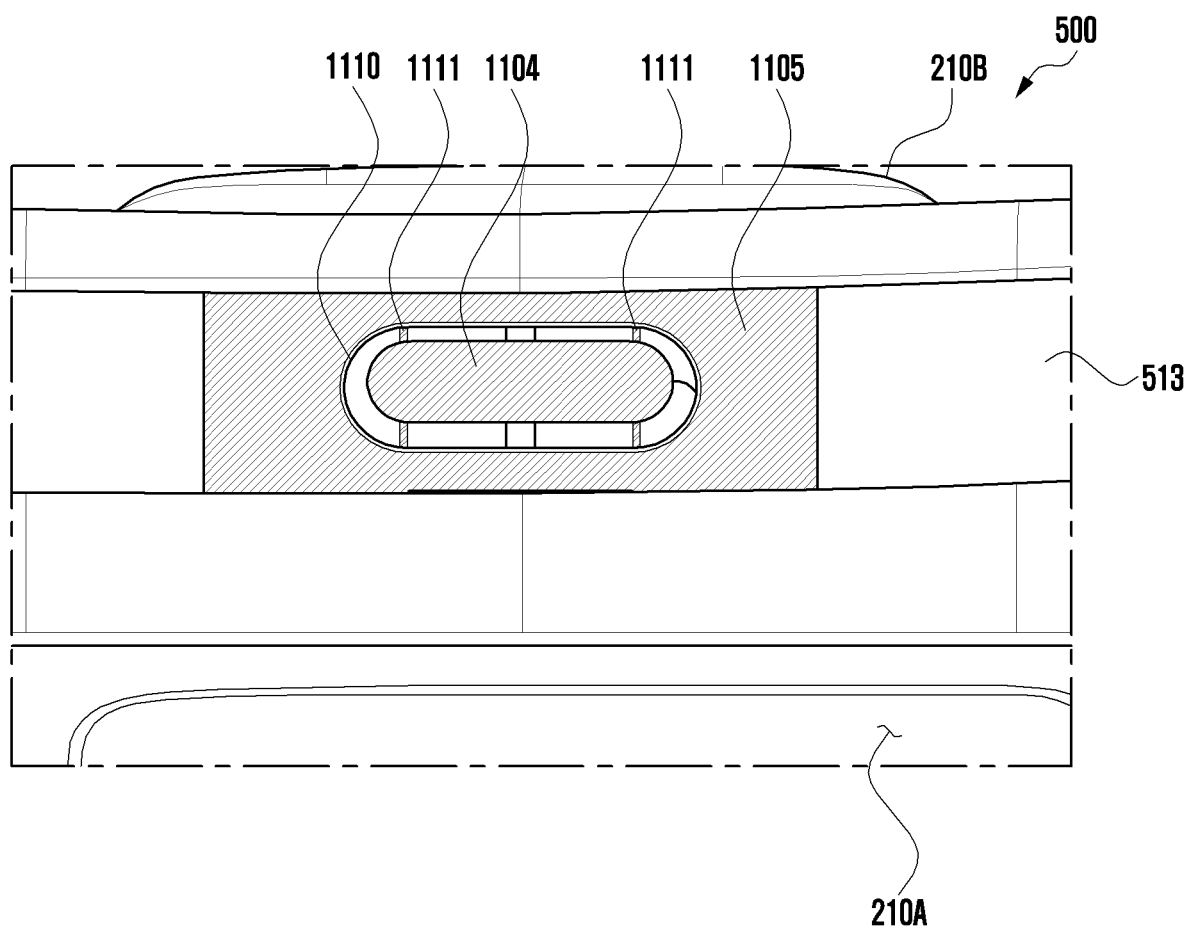

FIG. 11G illustrates a state in which at least one button 1110 is coupled to the side bezel structure 513 of the electronic device 500. With reference to FIG. 11G, the electronic device 500 may include a first surface (or front surface) 210A, a second surface (or rear surface) 210B, and a side bezel structure 513 enclosing a space between the first surface 210A and the second surface 210B. According to an embodiment, the electronic device 500 may include at least one button 1110 at least partially coupled to the side bezel structure 513. According to an embodiment, the at least one button 1110 may include a first conductive portion 1104 to correspond to an area exposed to the outside. For example, the first conductive portion 1104 may be formed in a form deposited or coated on the at least one button 1110. According to an embodiment, the side bezel structure 513 may include a second conductive portion 1105 adjacent to the first conductive portion 1104. According to an embodiment, the first conductive portion 1104 and the second conductive portion 1105 may be electrically coupled and used as one electrode. According to another embodiment, each of the first conductive portion 1104 and the second conductive portion 1105 may be independently used as different electrodes.

Figure 11H:
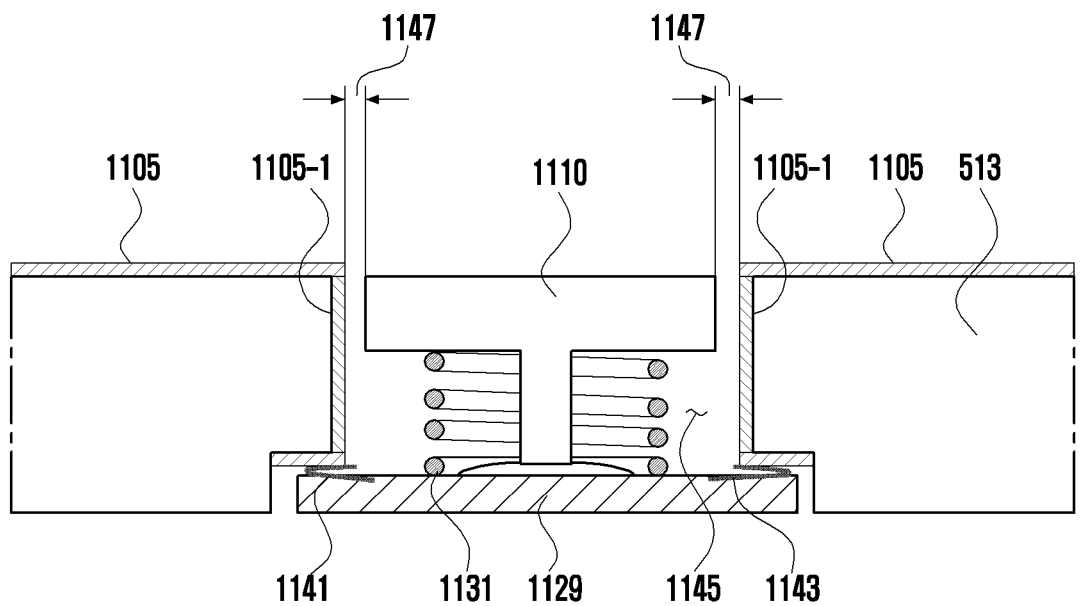

FIG. 11H is a cross-sectional view illustrating at least one button 1110 made of a conductive material. With reference to FIG. 11H, at least one button 1110 may be made of a conductive material and be used as one electrode. According to an embodiment, at least one button 1110 may be coupled to the side bezel structure 513. The side bezel structure 513 may include a coupling area to which the at least one button 1110 is coupled. For example, the coupling area may be an opening 1145. According to an embodiment, in the side bezel structure 513, a conductive material 1105 may be at least partially formed to correspond to an area exposed to the outside of the at least one button 1110. For example, the conductive material 1105 may be formed in a form deposited or coated on the side bezel structure 513. According to one embodiment, a gap 1147 may be formed between at least one button 1110 and the conductive material 1105 formed in the side bezel structure 513, and the at least one button 1110 and the conductive material 1105 may be used as different electrodes. According to one embodiment, the at least one button 1110 may be flexibly moved by a spring member 1131. According to one embodiment, the conductive material 1105 formed in the side bezel structure 513 may be electrically connected to a conductive member 1105-1 used as a path for transferring a biometric signal and be electrically connected to a printed circuit board 1129 (e.g., the dome key FPCB 1129 of FIG. 11C) based on conductive connecting members 1141 and 1143. According to one embodiment, the user's biometric signal may be transferred to the printed circuit board 1129 through at least one of the conductive material 1105 formed in the side bezel structure 513 and/or the at least one button 1110.

Figure 11I:
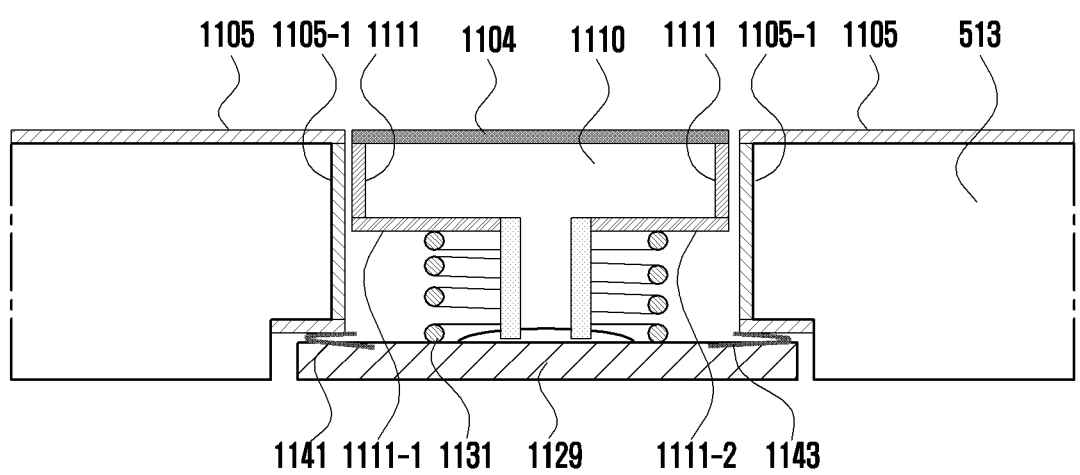

FIG. 11I is a cross-sectional view illustrating at least one button 1110 made of a non-conductive material. With reference to FIG. 11I, at least one button 1110 may be made of a non-conductive material, and a conductive material may be deposited or coated on some surfaces thereof. According to one embodiment, the at least one button 1110 may be at least partially enclosed by a conductive material. According to an embodiment, in at least one button 1110, a first conductive portion 1104 (e.g., conductive material) may be formed in at least a portion of an area exposed to the outside. According to one embodiment, in the side bezel structure 513 to which the at least one button 1110 is coupled, a second conductive portion 1105 (e.g., conductive material) may be formed to correspond to an area adjacent to the first conductive portion 1104. According to an embodiment, the first conductive portion 1104 may be electrically connected to conductive members 1111, 1111-1, and 1111-2 formed at least partially at a lower surface of the at least one button 1110. According to one embodiment, the first conductive portion 1104 may be electrically connected to a printed circuit board 1129 based on at least one of the conductive members 1111, 1111-1, and 1111-2 and/or a spring member 1131. According to one embodiment, the user's biometric signal may be transferred to the printed circuit board 1129 through the first conductive portion 1104, the conductive members 1111, 1111-1, and 1111-2, and/or the spring member 1131.

Figure 11J:
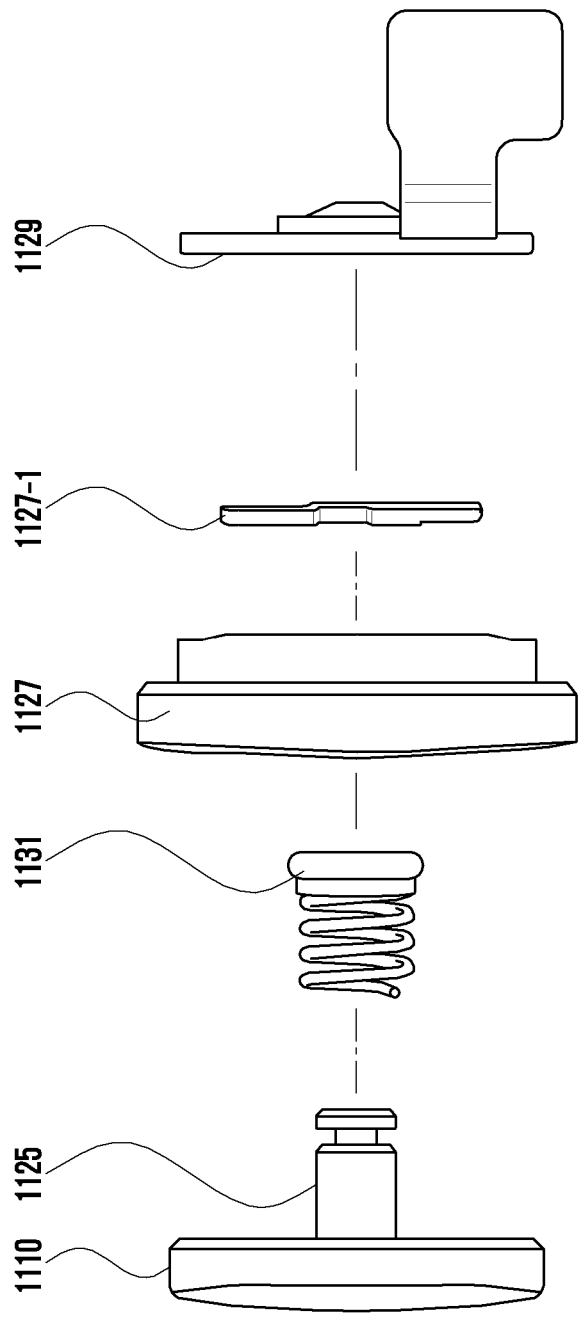

FIG. 11J illustrates another structure of at least one button 1110. With reference to FIG. 11J, a dome key FPCB 1129 may be formed such that at least one button 1110 is coupled to a spring member 1131 and support members 1127 and 1127-1. The at least one button 1110 may include at least partially a conductive member. According to an embodiment, the at least one button 1110 may be electrically connected to the support members 1127 and 1127-1. For example, the support members 1127 and 1127-1 may be made of a conductive material or may have a form in which the conductive material is at least partially deposited. According to one embodiment, the support members 1127 and 1127-1 may be electrically connected to a printed circuit board 1129 (e.g., FPCB). According to an embodiment, the at least one button 1110 may obtain a biometric signal of the user in response to the user's contact. According to an embodiment, the obtained biometric signal may be transferred to the printed circuit board 1129 through the support members 1127 and 1127-1 and/or the spring member 1131. According to an embodiment, the at least one button 1110 may further include a waterproof O-ring (e.g., the waterproof O-ring 1123 of FIG. 11C) to prevent external moisture from entering.

Figure 12A:
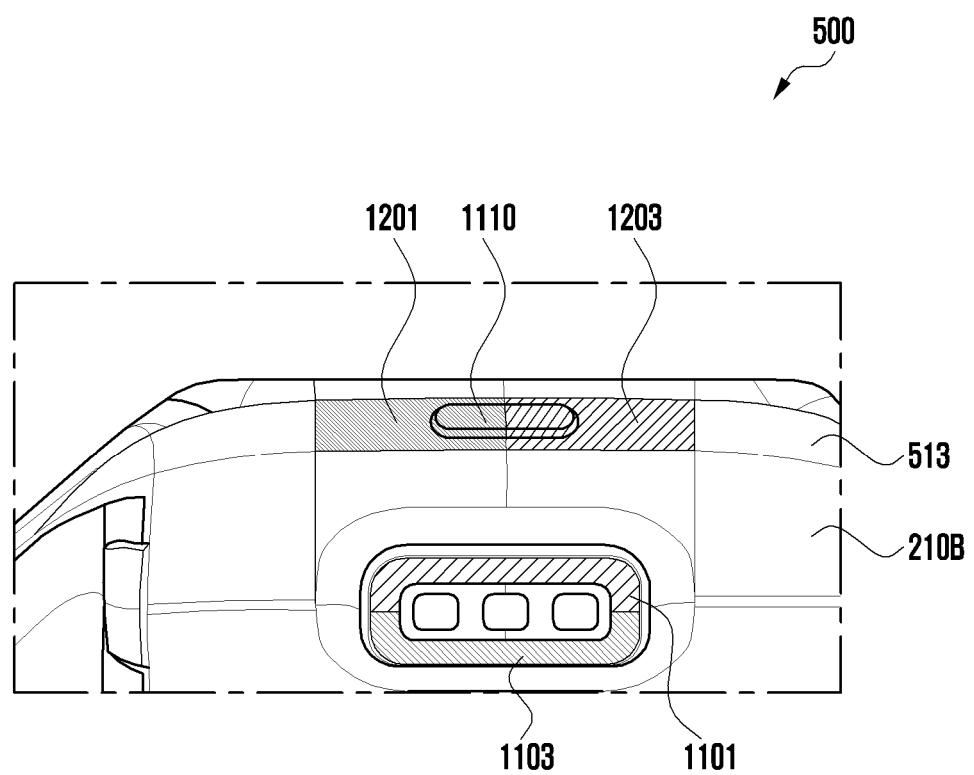
FIGS. 12A to 12C are diagrams illustrating a second embodiment of implementing a first conductive portion and a second conductive portion based on a button of an electronic device according to an embodiment of the disclosure.
Figure 12B:
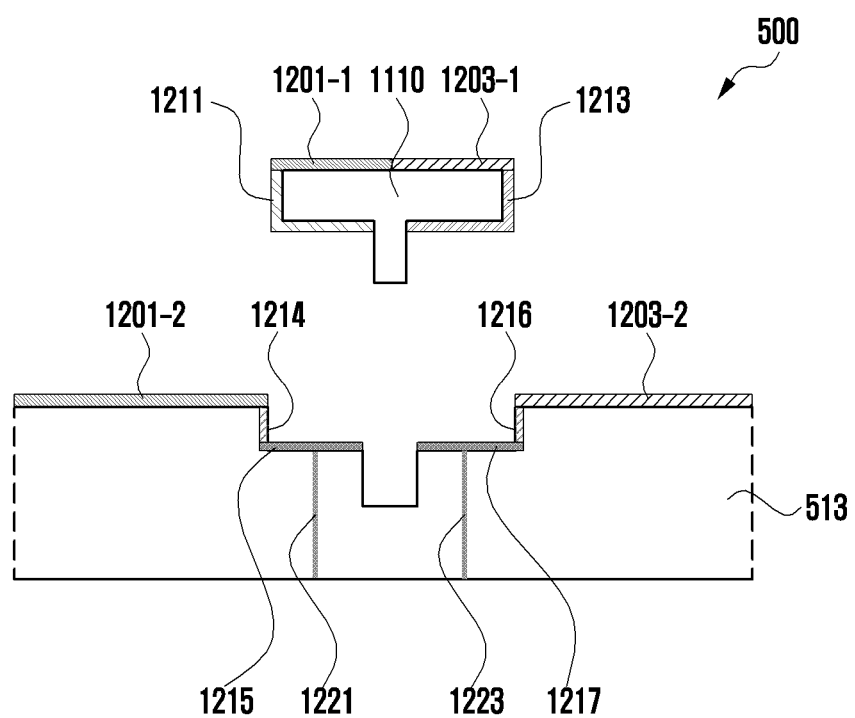
Figure 12C:
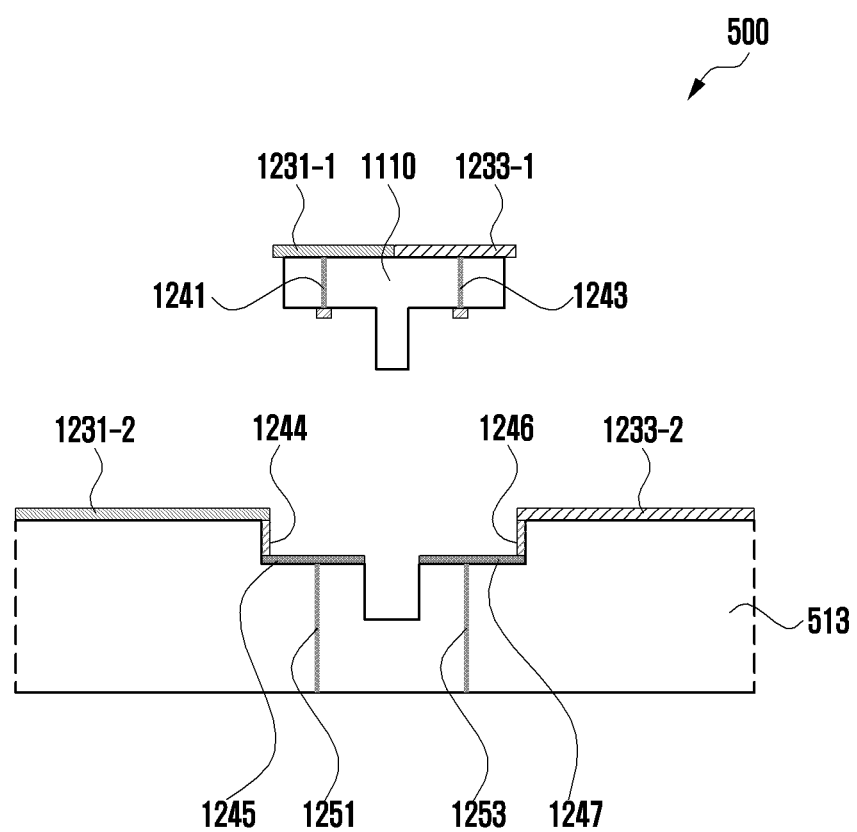

FIGS. 12A to 12C are diagrams illustrating a second embodiment of implementing a first conductive portion 1201 and a second conductive portion 1203 based on a button 1110 of an electronic device 500 according to an embodiment of the disclosure.

FIG. 12A illustrates a side bezel structure 513 and a rear surface 210B of at least a portion of the electronic device 500. FIGS. 12B to 12C are a cross-sectional view of a side bezel structure 513 to which at least one button 1110 is coupled.

With reference to FIG. 12A, the electronic device 500 may include at least one button 1110 disposed to be exposed from an internal space to the outside through at least a portion of the side bezel structure 513. According to an embodiment, the electronic device 500 may include a first conductive portion 1201 and a second conductive portion 1203 formed based on at least a portion of at least one button 1110 and the side bezel structure 513 around the button. According to an embodiment, the first conductive portion 1201 and the second conductive portion 1203 may have a short-circuited structure. As another example, the first conductive portion 1201 and the second conductive portion 1203 may be electrically separated. According to an embodiment, the electronic device 500 may include a third conductive portion 1101 and a fourth conductive portion 1103 at least partially formed in the rear surface 210B. According to an embodiment, the electronic device 500 may measure the user's electrocardiogram based on at least three of the first conductive portion 1201, the second conductive portion 1203, the third conductive portion 1101, and/or the fourth conductive portion 1103. For example, at least one of the first conductive portion 1201 and the second conductive portion 1203 may function as a positive (+) electrode, and at least one of the third conductive portion 1101 and the fourth conductive portion 1103 may function as a negative (−) electrode. A portion that does not function as a specific electrode among the first conductive portion 1201, the second conductive portion 1203, the third conductive portion 1101, and/or the fourth conductive portion 1103 may function as the ground (GND).

FIG. 12B illustrates a structure in which at least one button 1110 is disposed in the side bezel structure 513. According to one embodiment, the at least one button 1110 may be disposed in a form at least partially coupled to the side bezel structure 513. According to an embodiment, in the electronic device 500, first conductive portions 1201-1 and 1201-2 (e.g., the first conductive portion 1201 of FIG. 12A) and second conductive portions 1203-1 and 1203-2 (e.g., the second conductive portion 1203 of FIG. 12A) may be disposed based on at least a portion of the button 1110 and the side bezel structure 513 around the button. For example, the first conductive portions 1201-1 and 1201-2 may include a first area 1201-1 formed in at least one button 1110 and a first peripheral area 1201-2 adjacent to the first area 1201-1 and formed in the side bezel structure 513. The second conductive portions 1203-1 and 1203-2 may include a second area 1203-1 formed in the at least one button 1110 and a second peripheral area 1203-2 adjacent to the second area 1203-1 and formed in the side bezel structure 513. According to an embodiment, the first conductive portions 1201-1 and 1201-2 and the second conductive portions 1203-1 and 1203-2 may be in an electrically short-circuited state. As another example, the first conductive portions 1201-1 and 1201-2 and the second conductive portions 1203-1 and 1203-2 may be electrically separated.

According to an embodiment, the first conductive portions 1201-1 and 1201-2 and the second conductive portions 1203-1 and 1203-2 may function as one electrode, or may function as different electrodes, respectively. According to an embodiment, the first area 1201-1 of the first conductive portions 1201-1 and 1201-2 may be electrically connected to the printed circuit board based on a first conductive member 1211 that at least partially encloses at least one button 1110 and a first conductive pad 1215 and a 1-1 conductive member 1221 (e.g., a conductive path made of a conductive material) electrically connected to the first conductive member 1211. The second area 1201-2 of the first conductive portions 1201-1 and 1201-2 may be electrically connected to the printed circuit board based on a second conductive member 1214 formed at least partially in the side bezel structure 513 and the first conductive pad 1215 and the 1-1 conductive member 1221 electrically connected to the second conductive member 1214. According to one embodiment, the first area 1203-1 of the second conductive portions 1203-1 and 1203-2 may be electrically connected to the printed circuit board through a third conductive member 1213 that at least partially encloses at least one button 1110 and a second conductive pad 1217 and a 2-1 conductive member 1223 (e.g., a conductive path made of a conductive material) electrically connected to the third conductive member 1213. The second area 1203-2 of the second conductive portions 1203-1 and 1203-2 may be electrically connected to the printed circuit board (e.g., the printed circuit board 480 of FIG. 4) based on a fourth conductive member 1216 formed at least partially in the side bezel structure 513 and the second conductive pad 1217 and the 2-1 conductive member 1223 electrically connected to the fourth conductive member 1216.

With reference to FIG. 12C, in the electronic device 500, a first conductive portion (e.g., a first conductive portion 1201 of FIG. 12A) and/or a second conductive portion (e.g., the second conductive portion 1203 of FIG. 12A) may be disposed based on at least a portion of at least one button 1110 and the side bezel structure 513 around the button. For example, first conductive portions 1231-1 and 1231-2 may include a first area 1231-1 formed in at least one button 1110 and a first peripheral area 1231-2 adjacent to the first area 1231-1 and formed in the side bezel structure 513. Second conductive portions 1233-1 and 1233-2 may include a second area 1233-1 formed in at least one button 1110 and a second peripheral area 1233-2 adjacent to the second area 1233-1 and formed in the side bezel structure 513.

According to one embodiment, the first area 1231-1 and the second area 1233-1 disposed at the at least one button 1110 may be electrically connected to the printed circuit board through different conductive paths, respectively. According to an embodiment, the first area 1231-1 may be electrically connected to the printed circuit board through first paths 1241 and 1251. The first peripheral area 1231-2 may be electrically connected to the printed circuit board based on a first conductive member 1244, a first conductive pad 1245, and a first path 1251. According to one embodiment, the second area 1233-1 may be electrically connected to the printed circuit board through second paths 1243 and 1253. The second peripheral area 1233-2 may be electrically connected to the printed circuit board based on a second conductive member 1246, a second conductive pad 1247, and the second path 1253. According to an embodiment, the first paths 1241 and 1251 and/or the second paths 1243 and 1253 may include at least partially an LDS pattern.

According to various embodiments of the disclosure, an electronic device (e.g., the electronic device 500 of FIG. 8A) includes a housing (e.g., the housing 501 of FIG. 7) including a first cover member (e.g., the front plate 503 of FIG. 8A), a second cover member (e.g., the rear plate 505 of FIG. 8A) facing in a direction opposite to that of the first cover member 503, and a side member (e.g., the side bezel structure 513 of FIG. 8A) enclosing a space between the first cover member 503 and the second cover member 505; a support member (e.g., the support member 460 of FIG. 4) coupled to or formed integrally with the side member 513; a printed circuit board (e.g., the printed circuit board 480 of FIG. 8A) disposed in the space and including a biometric circuit (e.g., the biometric circuit 710 of FIG. 7); at least one button (e.g., at least one button 1110 of FIG. 11A) formed at least partially in a side member 513 of the housing 501 and electrically connected to the printed circuit board 480 through a conductive member; a first conductive portion (e.g., the first conductive portion 1114 of FIG. 11A) formed to correspond to an area exposed to the outside of the at least one button 1110; a second conductive portion (e.g., the second conductive portion 1105 of FIG. 11A) adjacent to the at least one button 1110 to enclose the at least one button 1110 and at least partially formed in the side member 513; a third conductive portion (e.g., the third conductive portion 610 of FIG. 6) and fourth conductive portion (e.g., the fourth conductive portion 620 of FIG. 6) disposed at least partially in the second cover member 505 and electrically connected to the printed circuit board 480; and a first conductive path disposed in the space and configured to electrically connect the biometric circuit 710 and the first conductive portion 1104 and a second conductive path formed on the support member to electrically connect the biometric circuit 710 and the second conductive portion 1105. The biometric circuit 710 receives a biometric signal based on the first conductive portion 1104, the second conductive portion 1105, the third conductive portion 1106, the fourth conductive portion 620, the first conductive path, and the second conductive path.

According to one embodiment, the biometric circuit 710 may further include an electrocardiogram (ECG) circuit, and the biometric circuit may receive a user's biometric signal based on the first conductive portion 1104, the second conductive portion 1105, the third conductive portion 610, and the fourth conductive portion 620 and measure the user's electrocardiogram based on the received biometric signal.

According to one embodiment, the biometric circuit 710 may receive a first biometric signal corresponding to a first polarity through at least one of the first conductive portion 1104 and the second conductive portion 1105, receive a second biometric signal corresponding to a second polarity through one of the third conductive portion 610 and the fourth conductive portion 620, and measure a user's electrocardiogram based on the received first biometric signal and second biometric signal.

According to one embodiment, the first conductive portion 1104 and the second conductive portion 1105 may be integrated to receive together the first biometric signal corresponding to the first polarity.

According to one embodiment, the first conductive portion 1104 and the second conductive portion 1105 may be formed in a form in which a conductive material is at least partially deposited or coated.

According to various embodiments of the disclosure, an electronic device (e.g., the electronic device 500 of FIG. 8A) includes a housing (e.g., the housing 501 of FIG. 7) including a first cover member (e.g., the front plate 503 of FIG. 8A), a second cover member (e.g., the rear plate 505 of FIG. 8A) facing in a direction opposite to that of the first cover member 503, and a side member (e.g., the side bezel structure 513 of FIG. 8A) enclosing a space between the first cover member 502 and the second cover member 505; a support member (e.g., the support member 460 of FIG. 4) coupled to or formed integrally with the side member 513; a printed circuit board (e.g., the printed circuit board 480 of FIG. 8A) disposed in the space and including a biometric circuit (e.g., the biometric circuit 710 of FIG. 7); at least one button (e.g., at least one button 1110 of FIG. 11A) formed at least partially in a side member 513 of the housing 501 and electrically connected to the printed circuit board 480 through a conductive member; a first conductive portion (e.g., the second conductive portion 1105 of FIG. 11A) adjacent to the at least one button 1110 to enclose the at least one button 1110 and at least partially formed in the side member 513; a second conductive portion (e.g., the third conductive portion 610 of FIG. 6) and third conductive portion (e.g., the forth conductive portion 620 of FIG. 6) disposed at least partially in the second cover member 505 and electrically connected to the printed circuit board 480; and a first conductive path disposed in the space and configured to electrically connect the biometric circuit 710 and the at least one button 1110 and a second conductive path formed on the support member to electrically connect the biometric circuit 710 and the second conductive portion 1105. The biometric circuit 710 receives a biometric signal based on the at least one button 1110, the second conductive portion 1105, the second conductive portion 610, the third conductive portion 620, the first conductive path, and the second conductive path.

According to one embodiment, the at least one button may be formed based on a metallic material.

An electronic device according to various embodiments of the disclosure may include a sensing area using at least one conductive member disposed in at least a portion of a housing. Extension of a sensing area of the biometric sensor may be induced by the size of the conductive member. Therefore, as the sensing area is extended, sensing accuracy can be improved. According to an embodiment, in the electronic device, the size of the sensing area may be extended, and the user's biometric information may be obtained based on the extended sensing area. According to an embodiment, the existing sensing area and the extended sensing area are separated, and each sensing area may perform a sensing function independently. Further, various effects that can be directly or indirectly identified through this document can be provided.

Although the present disclosure has been described with various embodiments, various changes and modifications may be suggested to one skilled in the art. It is intended that the present disclosure encompass such changes and modifications as fall within the scope of the appended claims.

What is claimed is:

1. An electronic device comprising:
a housing comprising window glass, a first cover member enclosing the window glass, a second cover member facing in a direction opposite to that of the first cover member, and a side member enclosing a space between the first cover member and the second cover member;
a support member coupled to or formed integrally with the side member;
a printed circuit board disposed in the space and comprising a biometric circuit;
a first conductive portion formed at least partially in at least one of the first cover member or the side member;
a second conductive portion adjacent to the first conductive portion, at least partially formed in the window glass, and electrically connected to the printed circuit board through a conductive member;
a third conductive portion and fourth conductive portion disposed at least partially in the second cover member and electrically connected to the printed circuit board; and
a first conductive path disposed in the space and configured to electrically connect the biometric circuit and the first conductive portion, and a second conductive path formed on the support member to electrically connect the biometric circuit and the second conductive portion,
wherein the biometric circuit is configured to receive a biometric signal based on the first conductive portion, the second conductive portion, the third conductive portion, the fourth conductive portion, the first conductive path, and the second conductive path.

2. The electronic device of claim 1, wherein:
the first conductive path comprises a conductive film, a conductive paste, and a conductive sheet, and
the second conductive path comprises a laser direct structuring (LDS) pattern.

3. The electronic device of claim 1, wherein:
the biometric circuit further comprises an electrocardiogram (ECG) circuit, and
the biometric circuit is further configured to:
receive a user's biometric signal based on the first conductive portion, the second conductive portion, the third conductive portion, and the fourth conductive portion, and
measure a user's electrocardiogram based on the received biometric signal.

4. The electronic device of claim 3, wherein the biometric circuit is further configured to:
- receive a first biometric signal corresponding to a first polarity through at least one of the first conductive portion and the second conductive portion;
- receive a second biometric signal corresponding to a second polarity through one of the third conductive portion and the fourth conductive portion; and
- measure a user's electrocardiogram based on the received first biometric signal and the received second biometric signal.

5. The electronic device of claim 4, wherein the first conductive portion and the second conductive portion are integrated to receive together the first biometric signal corresponding to the first polarity.

6. The electronic device of claim 1, wherein:
- an insulating member is disposed between the first conductive path and the second conductive path, and
- the first conductive path and the second conductive path are separately formed by the insulating member.

7. The electronic device of claim 1, wherein:
- the first conductive portion is formed to be at least partially deposited or coated on the window glass, and
- the second conductive portion is formed to be at least partially deposited or coated on at least one of the first cover member or the side member.

8. An electronic device comprising:
- a housing comprising a first cover member, a second cover member facing in a direction opposite to that of the first cover member, and a side member enclosing a space between the first cover member and the second cover member;
- a support member coupled to or formed integrally with the side member;
- a printed circuit board disposed in the space and comprising a biometric circuit;
- at least one button formed at least partially in a side member of the housing and electrically connected to the printed circuit board through a conductive member;
- a first conductive portion adjacent to the at least one button to enclose the at least one button and at least partially formed in the side member;
- a second conductive portion and third conductive portion disposed at least partially in the second cover member and electrically connected to the printed circuit board; and
- a first conductive path disposed in the space and configured to electrically connect the biometric circuit and the at least one button, and a second conductive path formed on the support member to electrically connect the biometric circuit and the first conductive portion,
- wherein the biometric circuit is configured to receive a biometric signal based on the at least one button, the first conductive portion, the second conductive portion, the third conductive portion, the first conductive path, and the second conductive path.

9. The electronic device of claim 8, wherein the at least one button is formed based on a metallic material.

10. The electronic device of claim 8, further comprising:
- a fourth conductive portion formed to correspond to an area exposed to an outside of the at least one button; and
- a third conductive path disposed in the space and configured to electrically connect the biometric circuit and the fourth conductive portion, and a fourth conductive path formed on the support member to electrically connect the biometric circuit and the first conductive portion,
- wherein the biometric circuit is configured to receive a biometric signal based on the at least one button, the first conductive portion, the second conductive portion, the third conductive portion, the fourth conductive portion, the first conductive path, and the second conductive path.

11. The electronic device of claim 10, wherein:
- the biometric circuit further comprises an electrocardiogram (ECG) circuit, and
- the biometric circuit is further configured to:
- receive a user's biometric signal based on the first conductive portion, the second conductive portion, the third conductive portion, and the fourth conductive portion, and
- measure a user's electrocardiogram based on the received biometric signal.

12. The electronic device of claim 11, wherein the biometric circuit is further configured to:
- receive a first biometric signal corresponding to a first polarity through at least one of the first conductive portion and the second conductive portion;
- receive a second biometric signal corresponding to a second polarity through one of the third conductive portion and the fourth conductive portion; and
- measure a user's electrocardiogram based on the received first biometric signal and the received second biometric signal.

13. The electronic device of claim 12, wherein the first conductive portion and the second conductive portion are integrated to receive together the first biometric signal corresponding to the first polarity.

14. The electronic device of claim 10, wherein the first conductive portion and the second conductive portion are formed in a form in which a conductive material is at least partially deposited or coated.

* * * * *